US008420696B2

(12) United States Patent
Weinstock-Rosin et al.

(10) Patent No.: US 8,420,696 B2
(45) Date of Patent: Apr. 16, 2013

(54) USE OF LOW-DOSE LADOSTIGIL FOR NEUROPROTECTION

(75) Inventors: Marta Weinstock-Rosin, Jerusalem (IL); Shai Shoham, Jerusalem (IL)

(73) Assignees: Yissum Research Development Company of the Hebrew University of Jerusalem, Jerusalem; Technion Research and Development Foundation Ltd., Haifa (IL)

( * ) Notice: Subject to any disclaimer, the term of this patent is extended or adjusted under 35 U.S.C. 154(b) by 1021 days.

(21) Appl. No.: 11/637,600

(22) Filed: Dec. 11, 2006

(65) Prior Publication Data
US 2007/0293583 A1 Dec. 20, 2007

Related U.S. Application Data

(60) Provisional application No. 60/792,410, filed on Apr. 17, 2006, provisional application No. 60/748,748, filed on Dec. 9, 2005.

(51) Int. Cl.
*A61K 31/27* (2006.01)
(52) U.S. Cl.
USPC .......................................................... 514/480
(58) Field of Classification Search .................. 514/480, 514/657, 551
See application file for complete search history.

(56) References Cited

U.S. PATENT DOCUMENTS

| | | | |
|---|---|---|---|
| 2,573,645 A | 10/1951 | Kerwin et al. | 260/570.6 |
| 2,916,490 A | 12/1959 | Schenck et al. | 260/247 |
| 2,982,783 A | 5/1961 | Schenck et al. | 260/571 |
| 3,060,091 A | 10/1962 | Witkin | 167/65 |
| 3,123,642 A | 3/1964 | Temple et al. | 260/567.6 |
| 3,178,478 A | 4/1965 | Huebner | 260/578 |
| 3,201,470 A | 8/1965 | Huebner | 260/577 |
| 3,253,037 A | 5/1966 | Huebner et al. | 260/577 |
| 3,308,157 A | 3/1967 | Robertson et al. | 260/562 |
| 3,507,962 A | 4/1970 | Taylor | 424/300 |
| 3,513,240 A | 5/1970 | Berardus et al. | 424/300 |
| 3,513,244 A | 5/1970 | Gittos et al. | 424/320 |
| 3,637,740 A | 1/1972 | Sarges | 260/326.5 |
| 3,704,323 A | 11/1972 | Krapcho | 260/576 |
| 3,709,996 A | 1/1973 | Gittos et al. | 424/330 |
| 3,751,420 A | 8/1973 | Hauck et al. | 260/293.56 |
| 3,804,898 A | 4/1974 | Panneman | 260/564 |
| 3,886,168 A | 5/1975 | Himmele et al. | 260/293.62 |
| 3,903,297 A | 9/1975 | Robert | 424/305 |
| 3,991,207 A | 11/1976 | Sarges et al. | 424/319 |
| 4,029,731 A | 6/1977 | Sarges | 424/316 |
| 4,096,173 A | 6/1978 | Molloy | 260/501.1 |
| 4,128,666 A | 12/1978 | Bondinell et al. | 424/330 |
| 4,132,737 A | 1/1979 | Molloy | 260/578 |
| 4,134,997 A | 1/1979 | Cannon et al. | 424/330 |
| 4,172,093 A | 10/1979 | Göransson-Dahlander et al. | 260/570.8 |
| 4,632,939 A | 12/1986 | Beedle et al. | 514/619 |
| 4,638,001 A | 1/1987 | Kuhla et al. | 514/212 |
| 4,788,130 A | 11/1988 | Oshiro et al. | 514/661 |
| 4,792,628 A | 12/1988 | Oshiro et al. | 564/428 |
| 4,826,875 A | 5/1989 | Chiesi | 514/534 |
| 4,833,273 A | 5/1989 | Goel | 564/304 |
| 4,873,241 A | 10/1989 | Napier et al. | 514/237.8 |
| 4,948,807 A | 8/1990 | Rosin et al. | 514/484 |
| 5,011,995 A | 4/1991 | Pugin et al. | 564/302 |
| 5,071,875 A | 12/1991 | Horn et al. | 514/613 |
| 5,118,704 A | 6/1992 | Minaskanian et al. | 514/416 |
| 5,134,147 A | 7/1992 | Peglion et al. | 514/300 |
| 5,153,225 A | 10/1992 | Schohe et al. | 514/602 |
| 5,189,045 A | 2/1993 | Peglion et al. | 514/319 |
| 5,196,583 A | 3/1993 | Yamada et al. | 564/305 |
| 5,225,596 A | 7/1993 | Carlsson et al. | 564/428 |
| 5,242,919 A | 9/1993 | Oshiro et al. | 514/227.5 |
| 5,273,974 A | 12/1993 | Goto et al. | 514/221 |
| 5,286,747 A | 2/1994 | Arvidsson et al. | 514/481 |
| 5,378,729 A | 1/1995 | Kohn et al. | 514/231.2 |
| 5,387,612 A | 2/1995 | Youdim et al. | 514/647 |
| 5,389,687 A | 2/1995 | Schaus et al. | 514/657 |
| 5,401,758 A | 3/1995 | Atwal et al. | 514/353 |
| 5,453,446 A | 9/1995 | Youdim et al. | 514/647 |
| 5,457,133 A | 10/1995 | Youdim et al. | 514/647 |
| 5,486,541 A | 1/1996 | Sterling et al. | 514/657 |
| 5,516,943 A | 5/1996 | Gao et al. | 564/444 |
| 5,519,061 A | 5/1996 | Youdim et al. | 514/647 |
| 5,532,415 A | 7/1996 | Youdim et al. | |

(Continued)

FOREIGN PATENT DOCUMENTS

EP 0 436 492 A2 7/1991
EP 0 538 134 B1 4/1993

(Continued)

OTHER PUBLICATIONS

Intelihealth, "Alzheimer's disease," online, accessed Jun. 30, 2008, http://www.intelihealth.com/IH/intIh/WSIHW000/8303/9117/195703.html?d=dmtHealthAZ.*
Intelihealth, "Dementia," online, accessed Sep. 22, 2009, http://www.intelihealth.com/IH/ihtIH/WSIHW000/24479/11184.html.*
Intelihealth, "Parkinson's disease," online, accessed Sep. 22, 2009, http://www.intelihealth.com/IH/ihtIH?d=dmtHealthAZ&c=201957.*
Moreira PI, Siedlak SL, Aliev G, Zhu X, Cash AD, Smith MA, and Perry G, "Oxidative stress mechanisms and potential therapeutics in Alzheimer disease," Journal of Neural Transmission, Jul. 2005, 112(7), 921-932 (Epub Dec. 7, 2004).*
Tyurin VA, Tyurina YY, Borisenko GG, Sokolova TV, Ritov VB, Quinn PJ, Rose M, Kochanek P, Graham SH, and Kagan VE, "Oxidative stress following traumatic brain injury in rats: quantitation of biomarkers and detection of free radical intermediates," Journal of Neurochemistry, Nov. 2000, 75(5), 2178-2189.*
Arnaiz, E. et al., (2001) Impaired cerebral glucose metabolism and cognitive functioning predict deterioration in mild cognitive impairment. Neuroreport 12(4):851-5.
Bartolini, L. et al., (1996) Aniracetam restores object recognition impaired by age, scopolamine, and nucleus basalis lesions. Pharmacol Biochem Behav. 53(2):277-83.

(Continued)

Primary Examiner — Paul Zarek
(74) Attorney, Agent, or Firm — Winston & Strawn LLP

(57) ABSTRACT

The subject invention provides a method of preventing a neurodegenerative disease in a subject or oxidative stress in the brain of a subject, comprising administering to the subject a less than cholinesterase-inhibitory amount or a less than monoamine oxidase-inhibitory amount of R(+)-6-(N-methyl, N-ethyl-carbamoyloxy)-N'-propargyl-1-aminoindan or a salt thereof effective to prevent the neurodegenerative disease or oxidative stress in the subject.

20 Claims, 7 Drawing Sheets

U.S. PATENT DOCUMENTS

| | | | |
|---|---|---|---|
| 5,569,669 A | 10/1996 | Guillaumet et al. | 514/432 |
| 5,576,353 A | 11/1996 | Youdim et al. | 514/647 |
| 5,602,176 A | 2/1997 | Enz | 514/490 |
| 5,639,913 A | 6/1997 | Lidor et al. | 564/304 |
| 5,646,188 A | 7/1997 | Gilad et al. | 514/634 |
| 5,654,301 A | 8/1997 | Kohn et al. | 514/231.2 |
| 5,668,181 A | 9/1997 | Youdim et al. | 514/657 |
| 5,708,018 A | 1/1998 | Haadsma-Svensson et al. | 514/408 |
| 5,744,500 A | 4/1998 | Youdim et al. | 514/647 |
| 5,786,390 A | 7/1998 | Youdim et al. | 514/657 |
| 5,844,003 A | 12/1998 | Tatton et al. | 514/654 |
| 5,877,218 A | 3/1999 | Herzig et al. | 514/617 |
| 5,877,221 A | 3/1999 | Cohen et al. | 514/629 |
| 5,880,159 A | 3/1999 | Herzig et al. | 514/625 |
| 5,891,923 A | 4/1999 | Youdim et al. | 514/657 |
| 5,914,349 A | 6/1999 | Cohen et al. | 514/613 |
| 5,994,408 A | 11/1999 | Cohen et al. | 514/657 |
| 6,251,938 B1 | 6/2001 | Chorev et al. | |
| 6,303,650 B1 | 10/2001 | Chorev et al. | 435/6 |
| 6,316,504 B1 | 11/2001 | Youdim et al. | |
| 6,462,222 B1 | 10/2002 | Chorev et al. | |
| 6,528,685 B2 | 3/2003 | Cohen et al. | 564/215 |
| 6,538,025 B2 | 3/2003 | Chorev | 514/480 |
| RE39,616 E | 5/2007 | Chorev et al. | |
| 2004/0010038 A1 | 1/2004 | Blaugrund et al. | |
| 2005/0065176 A1 | 3/2005 | Field | 514/214 |
| 2005/0267077 A1 | 12/2005 | Gallagher | 514/750 |
| 2006/0189685 A1 | 8/2006 | Licht et al. | |
| 2006/0189819 A1 | 8/2006 | Bahar | |
| 2006/0276537 A1 | 12/2006 | Goren | 514/482 |
| 2007/0135518 A1 | 6/2007 | Weinstock-Rosin et al. | |
| 2007/0203232 A1 | 8/2007 | Piryatinsky et al. | |
| 2007/0232691 A1 | 10/2007 | Goren et al. | |
| 2009/0131535 A1 | 5/2009 | Blaugrund | 514/657 |
| 2010/0093848 A1 | 4/2010 | Piryatinsky | 562/41 |

FOREIGN PATENT DOCUMENTS

| | | |
|---|---|---|
| EP | 0 614888 A1 | 9/1994 |
| EP | 0 664 291 A1 | 7/1995 |
| EP | 0 951 284 | 10/2003 |
| GB | 852735 | 11/1960 |
| GB | 1003686 | 9/1965 |
| HK | 1022838 | 7/2004 |
| JP | 3-2155 A | 1/1991 |
| WO | WO 9100724 A1 | 1/1991 |
| WO | WO 93/11761 A | 6/1993 |
| WO | WO 94/22495 A | 10/1994 |
| WO | WO 95/04027 A1 | 2/1995 |
| WO | WO 95/11016 A1 | 4/1995 |
| WO | WO 95/18617 | 7/1995 |
| WO | WO 96/02524 A1 | 2/1996 |
| WO | WO 96/37199 A1 | 11/1996 |
| WO | WO 97/07093 A1 | 2/1997 |
| WO | WO 97/12583 A2 | 4/1997 |
| WO | WO 98/02152 A1 | 1/1998 |
| WO | WO 98/27055 | 6/1998 |
| WO | WO 03/072055 | 9/2003 |
| WO | WO 2005/051371 | 6/2005 |
| WO | WO 2006/091656 | 8/2006 |
| WO | WO 2006/091836 | 8/2006 |
| WO | WO 2006/130726 | 12/2006 |
| WO | WO 2007/070425 | 6/2007 |
| WO | WO 2007/087029 | 8/2007 |
| WO | WO 2007/100583 | 9/2007 |

OTHER PUBLICATIONS

Bolanos, Juan P. et al., (2004) Regulation of glucose metabolism by nitrosative stress in neural cells. Mol Aspects Med. 25(1-2):61-73.

Buccafusco, J. J. et al., (2003) Potential Cognitive actions of (N-Propargly-(3R)-aminoindan-5-yl)-ethyl, methyl carbamate (TV3326), a novel neuroprotective agent, as assessed in old Rhesus monkeys in their performance of versions of a delayed matching task. Neuroscience 119:669-678.

Casu, Maria Antonietta et al., (2002) Aging causes a preferential loss of cholinergic innervation of characterized neocortical pyramidal neurons. Cereb Cortex 12(3):329-337.

Ellman, George L. et al., (1961) A new and rapid colorimetric determination of acetylcholinesterase activity. Biochem. Pharmacol. 7(2):88-95.

Finch, Caleb E. (2003) Neurons, glia, and plasticity in normal brain aging. Neurobiol. Aging 24:S123-7.

Good, Paul F. et al., (1996) Evidence of neuronal oxidative damage in Alzheimer's disease. Am J Pathol. 149(1):21-8.

Gordon, Christopher J. (1994) Thermoregulation in laboratory mammals and humans exposed to anti-cholinesterase agents. Neurotoxicol. Teratol. 16(5):427-453.

Griffin, W. S. T. et al., (1998) Glial-neuronal interactions in Alzheimer's disease: the potential role of a 'cytokine cycle' in disease progression. Brain Pathol. 8(1):65-72.

Hensley, K. et al., in "Neuroinflammation: mechanisms and management" (Ed: P. L. Wood), Humana Press Inc., 1997.

Kielian, Tammy and Esen, Nilufer (2004) Effects of neuroinflammation on glia-glia gap junctional intercellular communication: a perspective. Neurochem Int. 45(2-3):429-36.

Lannert, Heinrich and Hoyer, Siegfried (1998) Intracerebroventricular administration of streptozotocin causes long-term diminutions in learning and memory abilities and in cerebral energy metabolism in adult rats. Behav Neurosci.112(5):1199-1208.

Lipton, Stuart A. and Rosenbrg, Paul A.(1994) Excitatory amino acids as a final common pathway for neurological disorders N Engl J Med. 330(9):613-22.

Maruayma, Wakako et al., (2003) Anti-apoptotic action of anti-Alzheimer drug, TV3326 [(N-propargyl)-(3R)-aminoindant-5-yl]-ethyl methyl carbamate, a novel cholinesterase-monoamine oxidase inhibitor. Neurosci Lett. 341(3):233-236.

Mattson, Mark P. et al., (1997) Activation of NF-κB protects hippocampal neurons against oxidative stress-induced apoptosis: Evidence for induction of manganese superoxide dismutase and suppression of peroxynitrite production and protein tyrosine nitration. J Neurosci Res. 49(6):681-697.

McCarty, Mark F. (2006) Down-regulation of microglial activation may represent a practical strategy for combating neurodegenerative disorders. Med Hypotheses 67(2):251-269.

McGeer, Edith G. and McGeer, Patick L. (2003) Inflammatory processes in Alzheimer's disease. Prog. Neuro-Psychopharmacol. Biol. Psychiatry 27(5):741-9.

Mealy et al., (2004) "Ladostigil Hemitartrate", Drugs of the Future, abstract 2004176769 29(3), 293.

Meyer, John Stirling et al., (2005) MRI Abnormalities Associated with Mild Cognitive Impairments of Vascular (VMCI) Versus Neurodegenerative (NMCI) Types Prodromal for Vascular and Alzheimer's Dementias. Curr Alz Res 2(5):579-585.

Miguel-Hidalgo, J. J. et al., (2002) Neuroprotection by memantine against neurodegeneration induced by beta-amyloid (1-40), Brain Res. 958(1):210-221.

Mumby, Dave G. et al., (2002) Hippocampal damage and exploratory preferences in rats: memory for objects, places, and contexts. Learn Mem. 9(2):49-57.

Nitch, R. et al., (1989) The intracerebroventricularly streptozotocin-treated rat: impairment of cerebral glucose metabolism resembles the alterations of carbohydrate metabolism of the brain in Alzheimer's disease, J. Neural Transm. P-D sect 1(1-2):109-10.

Ouyang, Yi-Bing and Giffard, Rona G. (2004) Changes in astrocyte mitochondrial function with stress: effects of Bcl-2 family proteins. Neurochem Int. 45(2-3):371-9.

Petersen, Ronald C. et al., (2001) Current concepts in mild cognitive impairment. Arch Neurol. 58(12):1985-92.

Poltyrev, Tatyana et al., (2005) Effect of chronic treatment with ladostigil (TV-3326) on anxiogenic and depressive-like behaviour and on activity of the hypothalamic-pituitary-adrenal axis in male and female prenatally stressed rats. Psychopharmacology (Berl) 181(1):118-125.

Sagi, Yotam et al., (2003) Attenuation of MPTP-induced dopaminergic neurotoxicity by TV3326, a cholinesterase-monoamine oxidase inhibitor. J Neurochem. 86:290-297.

Sagi, Yotam et al., (2005) The neurochemical and behavioural effects of the novel cholinesterase-monoamine oxidase inhibitor, ladostigil, in response to L-dopa and L-tryptophan, in rats. Br J Pharmacol. 146(4):553-60.

Scali, C. et al., (2002) Effect of subchronic administration of metrifonate, rivastigmine and donepezil on brain acetylcholine in aged F344 rats. J. Neural Transm. 109(7-8):1067-1080.

Sharma, Monisha and Gupta, Y. K. (2001) Effect of chronic treatment of melatonin on learning, memory and oxidative deficiencies induced by intracerebroventricular streptozotocin in rats. Pharmacol Biochem Behav 70(2-3):325-331.

Sharma, Monish and Gupta, Y. K. (2002) Chronic treatment with trans resveratrol prevents intracerebroventricular streptozotocin induced cognitive impairment and oxidative stress in rats. Life Sci 71(21):2489-2498.

Shoham, S. et al., (2003) Intracerebroventricular injection of streptozotocin causes neurotoxicity to myelin that contributes to spatial memory deficits in rats. Exp Neurol. 184(2):1043-52.

Shoham, Shai et al., (2007) Ladostigil prevents gliosis, oxidative-nitrative stress and memory deficits induced by intracerebroventricular injection of streptozotocin in rats. Neuropharmacol 52(3):836-843 (Epub Nov. 22, 2006).

Shytle, R. Douglas et al., (2004) Cholinergic modulation of microglial activation by alpha 7 nicotinic receptors. J Neurochem. 89(2):337-43.

Simmons, Martha L. and Murphy, Sean (1992) Induction of nitric oxide synthase in glial cells. J Neurochem. 59(3):897-905.

Sterling, Jeffrey et al., (2002) Novel dual inhibitors of AChE and MAO derived from hydroxy Aminoindan and phenethylamine as potential treatment for Alzheimer's disease. J Med. Chem. 45(24):5260-5279.

Takasu, N. et al., (1991) Streptozocin- and alloxan-induced $H_2O_2$ generation and DNA fragmentation in pancreatic islets. $H_2O_2$ as mediator for DNA fragmentation. Diabetes. 40(9):1141-5.

Takuma, Kazuhiro et al., (2004) Astrocyte apoptosis: implications for neuroprotection. Prog Neurobiol. 72(2):111-127.

Turrini, P. et al., (2001) Cholinergic nerve terminals establish classical synapses in the rat cerebral cortex: synaptic pattern and age-related atrophy. Neurosci. 105(2):277-285.

Wahlgren, N. G. in R. Green, "International Review of Neurobiology: Neuroprotective Agents and Cerebral Ischemia", vol. 40, Academic Press, 1997.

Wang, R. H. et al., (2000) Gender differences in the effect of rivastigmine on brain cholinesterase activity and cognitive function in rats. Neuropharmacology 39(3):497-506.

Weinstock, M. et al. (2000) TV3326, a novel neuroprotective drug with cholinesterase and monoamine oxidase inhibitory activities for the treatment of Alzheimer's disease. J Neural Transm. Suppl. 60:157-69.

Weinstock, M. et al., (2000) Development of a novel neuroprotective drug (TV3326) for the treatment of Alzheimer's disease, with cholinesterase and monoamine oxidase inhibitory activities. Drug Dev. Res. 50: 216-222.

Weinstock, Marta et al., (2001) Neuroprotective Effects of Novel Cholinesterase Inhibitors Derived from Rasagiline as Potential Anti-Alzheimer Drugs. Ann. N.Y. Acad. Sci. 939:148-161.

Weinstock, M. et al., (2002) Limited potentiation of blood pressure response to oral tyramine by brain-selective monoamine oxidase A-B inhibitor, TV-3326 in conscious rabbits. Neuropharmacology 43(6):999-1005.

Weinstock, Marta et al., (2002) Effect of TV3326, a novel monoamine-oxidase cholinesterase inhibitor, in rat models of anxiety and depression, Psychopharmacology. 160(3):318-324.

Weinstock, M. et al., (2003) A novel cholinesterase and brain-selective monoamine oxidase inhibitor for the treatment of dementia co-morbid with depression and Parkinson's disease. Prog. Neuropsychopharmacol. Biol. Psychiatry 27: 555-561.

Winters, et al., (2004) Double dissociation between the effects of peri-postrhinal cortex and hippocampal lesions on tests of object recognition and spatial memory: heterogeneity of function within the temporal lobe, J. Neuroscience 24:5901-8.

Yogev-Falach, Merav et al., (2002) Involvement of MAP kinase in the regulation ofamyloid precursor protein processing by novel cholinesterase inhibitors derived from rasagiline. FASEB 16:1674-1676.

Yogev-Falach, Merav et al., (2006) A multifunctional, neuroprotective drug, ladostigil (TV3326), regulates holo-APP translation and processing. FASEB 20:E1610-E1618.

Youdim, Moussa B. H. and Weinstock, Marta (2001) Molecular Basis of Neuroprotective Activities of Rasagiline and the Anti-Alzheimer Drug TV3326 [Ipar;N-Propargyl-(3R) Aminoindan-5-YL)-Ethyl Methyl Carbamate] Cell Mol Neurobiol. 21(6):555-73.

Youdim, Moussa B. H. and Weinstock, Marta (2002) Novel neuroprotective anti-Alzheimer drugs with anti-depressant activity derived from the anti-Parkinson drug, rasagiline. Mechanisms of Ageing and Development 123 (2002) 1081-1086.

Youdim, Moussa B. H. et al., (2003) Amyloid processing and signal transduction properties of antiparkinson-antialzheimer neuroprotective drugs Rasagiline and TV3326. Ann. N.Y. Acad Sci 993:378-386.

Youdim, Moussa B. H. and Weinstock, Marta (2004) Therapeutic applications of selective and non-selective inhibitors of monoamine oxidase A and B that do not cause significant Tyramine potentiation. Neurotoxicology 25:243-250.

Youdim, Moussa B. H. et al., (2005) Rasagiline: Neurodegeneration, Neuroprotection, and Mitochondrial permeability transition. Journal of Neuroscience Research 79:172-179.

Chemical Abstract Service, (Columbus Ohio), Registry No. 209394-46-7.

Physician's Desk Reference, 59.sup.th Ed. (2005) pp. 1583-1584.

Mild Cognitive Impairment-Alzheimer's Part XVI, Harold Rubin, MS, ABD, CRC, Nov. 14, 2006.

Guidance for Industry: Estimating the Maximum Safe Starting Dose in Initial Clinical Trials for Therapeutics in Adult Healthy Volunteers, U.S. Dept. HHS/FDA/CDER (Jul. 2005), at http://www.fda.gov/cder/guidance/5541fnl.doc.

U.S. Appl. No. 11/635,922 Requirement for Restriction/Election dated May 13, 2009.

U.S. Appl. No. 11/635,922 Non-Final Rejection dated Oct. 15, 2009.

International Search Report of PCT/US2006/047038 mailed Dec. 11, 2007.

International Preliminary Examination Report of PCT/US2006/047038 mailed Dec. 11, 2007.

U.S. Appl. No. 60/656,866, filed Feb. 24, 2005, Bahar, Eliezer.

U.S. Appl. No. 60/686,791, filed Jun. 1, 2005, Goren, Tamar.

U.S. Appl. No. 60/700,850, filed Jul. 19, 2005, Goren, Tamar.

Chen, Yun et al., (1998) Cerebro-protective effects of ENA713, a novel acetylcholinesterase inhibitor, in closed head inlay in the rat. *Brain Research* 784:18-24.

Parikh, "Granule growth mechanisms and granulation characteristics", Handbook of pharmaceutical granulation technology, 1997 pp. 160-165.

Rosen, Wilma G. et al., (1984) A new rating scale for Alzheimer's disease. Am J Psychiatry 141:1356-1364.

"USP and NF excipients" The United States Pharmacopeia and The National Formulary, 2004, pp. 2809-2812.

Weinstock, M. et al., (2005) Ladostigil attenuates Gliosis and prevents oxidative-nitrative stress in hippocampus and memory deficits induced in rats by intracerebroventricular injection of streptozotocin. Reviews in the Neurosciences, Tel-Aviv, Israel16(suppl):S67.

Weinstock, M. and Shoham, S. (2004) Rat models of dementia based on reductions in regional glucose metabolism, cerebral blood flow and cytochrome oxidase activity. J Neural Trans. 111(3):347-366.

U.S. Appl. No. 11/635,922 Non-Final Rejection Oct. 15, 2009.

U.S. Appl. No. 11/635,922 Final Rejection Jun. 8, 2010.

U.S. Appl. No. 11/361,379 Request for Restriction/Election May 14, 2008.

U.S. Appl. No. 11/361,379 Non-Final Rejection Oct. 30, 2008.

U.S. Appl. No. 11/361,379 Final Rejection Apr. 15, 2010.

U.S. Appl. No. 11/361,379 Advisory action Jun. 30, 2010.

U.S. Appl. No. 11/361,379 Non-Final Rejection Aug. 3, 2010.

Feldman et al., Effect of rivastigmine on delay to diagnosis of Alzheimer's disease from mild cognitive impairment, . Lancet Neurology, vol. 6, pp. 501-512 (2007).

Chen, Yun et al., "Rivastigmine, a Brain-Selective Acetylcholinesterase Inhibitor, Ameliorates Cognitive and Motor Deficits Induced by Closed-Head Injuriy in the Mouse", Journal of Neurotrauma, vol. 15, No. 4, pp. 231-237 with Reference page (1998).

Armstrong et al., "Acylation effects on chiral recognition of racemic amines and alcohols by new polar and non-polar cyclodextrin derivative gas chromatographic phases," J. Chromatography 502: 154-159 (1990).

Askin et al., "Highly Diastereoselective Alkylations of Chiral Amide Enolates: New Routes to Hydroxyethylene Dipeptide Isostere Inhibitors of HIV-1 Protease," J. Org. Chem. 57:2771-2773 (1992).

Baker et al., "Synthesis of decahydrocyclopentacyclo-octene derivatives via intramolecular photocycloaddition of $\Delta^{\alpha,\beta}$-butenolides and reductive cleavage," J. Chem. Soc., Chem. Commun. 23:1011-1012 (1980).

Barton et al., "Reductive Formylation of Oximes; An Approach to the Synthesis of Vinyl Isonitriles," Tetrahedron Letters 29(27):3343-3346 (1988).

Barker et al., "Principles of Ambulatory Medicine, Fourth Edition," Williams & Wilkins publishers, 4:1240-1257 (1995).

Bentue-Ferrer et al., "Monoamine Oxidase B Inhibitors," CNS Drugs 6(3):217-236 (1996).

Boar et al., "A Simple Synthesis of Enamides from Ketoximes," J. Chem. Soc., Perkins 1, pp. 1237-1241 (1975).

Boltshauser et al., "Vanishing white matter and ovarian dysgenesis in an infant with cerebro-oculofacio-skeletal phenotype," Neuropediatrics 33(2):57-62 (2002).

Brettle et al., "Synthesis of Enamides," J. Chem. Soc., Perkin Trans. 1, pp. 2185-2195 (1988).

Burk et al., "A Three-Step Procedure for Asymmetric Catalytic Reductive Amidation of Ketones," J. Org. Chem. 63(18):6084-6085 (1998).

Chorvat et al., "Acetylcholine release enhancing agents: potential therapeutics for Alzheimer's disease," Drugs of the Future 20(11): 1145-1162 (1995).

Chrisp et al., "Selegiline: A Review of its Pharmacology, Symptomatic Benefits and Protective Potential in Parkinson's Disease," Drugs & Aging 1(3):228-248 (1991).

Chumpradit et al., "Synthesis and Optical Resolution of (R)- and (S)-trans-7-Hydroxy-2-[N-propyl-N (3'-iodo-2'-propenyl)amino]tetralin: A New D3 Dopamine Receptor Ligand," J. Med. Chem. 36:4308-4312 (1993).

Chumpradit et al., "Synthesis, resolution and radioiodination of S(−)trans-5-hydroxy-2-[N-n-propyl-N-(3'-iodo-2'-propenyl)amino]tetralin-S (−)trans-5-OH-PIPAT: A new dopamine D2-like receptor ligand," Journal of Labelled Compounds and Radiopharmaceuticals 36(11):1051-1062 (1995) (abstract only).

Cooper et al., "Alzheimer's Disease Drug Treatment" Journal of Geriatric Drug Therapy 8(2):5-18 (1993).

Cutler et al., "Muscarinic M1-Receptor Agonists: Potential in the Treatment of Alzheimer's Disease," CNS Drugs 3(6):467-481 (1995).

Davis et al., "Tacrine," The Lancet 345:625-630 (1995).

Delgado et al., "Wilson and Gisvold's Textbook of Organic Medicinal and Pharmaceutical Chemistry, Ninth Edition," J.B. Lippincott Company publishers, pp. 556-561(1995).

Dostert, "Can our knowledge of monoamine oxidase (MAO) help in the design of better MAO inhibitors?," J Neural Transm41:269-279 (1994).

Drefahl et al., "Amino alcohols. 1. Cis- and trans-DL-1-amino-2-hydroxytetrahydronaphthalene and cis- and trans-DL-1-amino-2-hydroxyindan," Che. Abstract 52: 16417f (1958).

Drefahl et al., "Amino Alcohols. X. Addition of iodine isocyanate to unsymmetrical olefins," Che. Abstracts 54: 13078f (1960).

Dutta et al., "Synthesis and Characterization of Novel Derivatives of2-Aminotetralins: Development of Highly Selective Derivatives for the D3 Receptor," Medicinal Chemistry Research 10(4):208-229 (2000).

Finberg et al., "Modification of blood pressure and nictitating membrane response to sympathetic amines by selective monoamine oxidase inhibitors, types A and B, in the cat," Br J Pharmacol. 85(2):541-546 (1985).

Fink et al., "Imino 1,2,3,4-tetrahydrocyclopent[b]indole carbamates as dual inhibitors of acetylcholinesterase and monoamine oxidase," Bioorganic & Medicinal Chemistry Letters 6(6):625-630 (1996).

Fitton et al., "Moclobemide: A Review of its Pharmacological Properties and Therapeutic Use in Depressive Illness," Drugs 43(4):561-596 (1992).

Florvall et al., "Prodrugs of neuron-selective monoamine oxidase inhibitors: amino acid derivatives of 1-(4-aminophenyl)-2-aminopropanes," Eur. J. Med. Chem 34:137-151 (1999).

Fuller et al., "Inhibition in vitro of norepinephrine N-methyltransferase by 2-aminotetralins, analogs of phenylethylamines with rigid conformation," Biochem Pharmacol. 26(5):446-447 (1976).

Gabryel et al., "Nootropics: pharmacological properties and therapeutic use," Pol J Pharmacol. 46(5):383-394 (1994).

Ghislandi et al., "Scissione Ottica E Configurazione Dell'l-Aminobenzociclobutene E Dell'l-Aminoindano," Boll. Chim. Farm. 115:489-500 (1976).

Harvey, "The Pharmacology of Galantamine and its Analogues," Pharmac. Ther. 68(1):113-128 (1995).

Hazelhoff et al., "N-methyl,N-propargyl-2-aminotetralins: Novel dopamine agonists with monoamine oxidase inhibiting properties," European Journal of Pharmacology 109(2):229-240 (1985).

Hazelhoff et al., "The neuropharmacological profile ofN-methyl-N-propargyl-2-aminotetralin: a potent monoamine oxidase inhibitor," Naunyn-Schmiedeberg's Arch PharmacoI330:50-58 (1985).

Heikkila et al., "Prevention of MPTP-induced neurotoxicity by AGN-1133 and AGN-1135, selective inhibitors of monoamine oxidase-B," European Journal of Pharmacology 116(3):313-317 (1985).

Hori et al., "N-containing diphenylethylamine derivatives and acid adducts", Japan Kokai Tokyo Koho JP 54-132559, Oct. 15, 1979, Database CAPLUS on STN®, Chemical Abstracts Service, (Columbus, Ohio), Accession No. 1980:180807, abstract.

Horn et al., "Brain Levels and Metabolism of the Dopaminergic Agonist 2-Amino-6,7-dihydroxytetrahydronaphthaline After Administration of Various Prodrugs," J. Med. Chem. 25(8):993-996 (1982).

Horn et al., "Steric Requirements for Catecholamine Uptake by Rat Brain Synaptosomes: Studies with Rigid Analogs of Amphetamine," Journal of Pharmacology and Experimental Therapeutics 180(3):523-530 (1972).

Huebner, "1-(N-Methyl-N-propargylamino)indans and related compounds," Chem. Abstracts 61:3046a (1964).

Jovan et al., "A retrospective chart review of risperidone use in treatment-resistant children and adolescents with psychiatric disorders," Progress in Neuro-Psychopharmacology and Biological Psychiatry 26(2):267-275 (2002).

Kabins et al., "Potential Applications for Monoamine Oxidase B Inhibitors," Dementia 1:323-348 (1990).

Kametani et al., "Studies on the Syntheses of Heterocyclic Compounds. CLIX. The Reaction of2-Nitro-1-indanone Oxime with Formalin and Hydrochloric Acid," Chem. Pharm. Bull. 14(12):1408-1413 (1966).

Knapp et al., "A 30-Week Randomized Controlled Trial of High-Dose Tacrine in Patients with Alzheimer's Disease," JAMA 271(13):985-991 (1994).

Kragten et al., "Glyceraldehyde-3-phosphate Dehydrogenase, the Putative Target of the Antiapoptotic Compounds CGP 3466 andR-(−)-Deprenyl," The Journal of Biological Chemistry 273(10):5821-5828 (1998).

Laso et al., "A New Selective Reduction of Nitroalkenes into Enamides," Tetrahedron Letters 37(10):1605-1608 (1996).

Lidor et al., "A Facile Synthesis for Racemic and Optically Active 1-Aminoindans," Organic Preparations and Procedures International (OPPI) 29(6):701-706 (1997).

Loscher et al., "Inhibition of Monoamine Oxidase Type A, but Not Type B, is an Effective Means of Inducing Anticonvulsant Activity in the Kindling Model of Epilepsy," Journal of Pharmacology and Experimental Therapeutics 288(3):984-992 (1999).

Martin et al., "Potential Anti-Parkinson Drugs Designed by Receptor Mapping," J Med Chem 16(2):147-150 (1973).

Martin et al., "Discriminant Analysis of the Relationship between Physical Properties and the Inhibition of Monoamine Oxidase by Aminotetralins and Aminoindans," J Med Chem 17(4):409-413 (1974).

Mouna et al., "Enantioselective Acetylation of Primary Amines by Cylindrocarpon Radiciola," Bioorg. Med. Chem. Lett. 3(4):681-684 (1993).

Nakamura, "Aniracetam: its novel therapeutic potential in cerebral dysfunctional disorders based on recent pharmacological discoveries," CNS Drug Rev. 8(1):70-89 (2002).

Nakanishi et al., "Preparation of Enamides via Reductive Acylation of N-Acetoxyimino Compounds by Use of $Fe_3(CO)_{12}$," Chemistry Letters 16(11):2167-2168 (1987).

O'Malley et al., "Synthesis and Biological Evaluation of Combined Acetyl Cholinesterase (AChE) and Monoamine Oxidase (MAO) Inhibitors," 205th ACS Mtg. (MEDI), abstract 78 (1993).

Oshiro et al., "Novel Cerebroprotective Agents with Central Nervous System Stimulating Activity. 1. Synthesis and Pharmacology of 1-Amino-7-Hydroxyindan Derivatives," J Med Chem 34(7):2004-2013 (1991).

Palermo et al., "Combined Acetylcholinesterase (AChE) and Reversible Monoamine Oxidase (MAO) Inhibition as Potential Therapeutic Approach for Senile Dementia of the Alzheimer Type (SADT)," 205th ACS Mtg. (MEDI), abstract 77 (1993).

Palfreyman et al., "Inhibition of Monoamine Oxidase Selectively in Brain Monoamine Nerves Using C55 the Bioprecursor (E-β-Fluoromethylene-m-Tyrosine (MDL 72394), a Substrate for Aromatic LAmino Acid Decarboxylase," Journal of Neurochemistry 45(6):1850-1860 (1985).

Riederer et al., "Monoamine Oxidase Activity and Monoamine Metabolism in Brains of Parkinsonian Patients Treated with 1-Deprenyl," Journal of Neurochemistry 46(5):1359-1365 (1986).

Ruschig et al., "Preparation of 17a-hydroxy-20-keto steroids from 17(20)-en-20-acetamino steroids," Chem. Ber. 88(6):883-894 (1955).

Semerci et al., "Cerebro-oculo-facio-skeletal syndrome: report of two cases from Turkey with postmortem findings," Turkish Journal of Pediatrics 44(3):269-273 (2002).

Silverman, "The Organic Chemistry of Drug Design and Drug Action," pp. 15-20 (1992).

Singh et al., "Antimalarials. 7-Chloro-4-(substituted amino)quinolines," J Med Chem 14(4):283-286 (1971).

Smith et al., "Quality Improvement of Painful Peripheral Neuropathy," Seminars in Oncology Nursing 18(1):36-43 (2002).

Speiser et al., "Effect of chronic treatment with ladostigil (TV-3326) on anxiogenic and depressive-C62 like behaviour and on activity of the hypothalamic-pituitary-adrenal axis in male and female prenatally stressed rats," Pharmacology (Bed), Apr. 14, 2005 (abstract).

Sramek et al., "Safety/Tolerability Trial of SDZ ENA 713 in patients with Probable Alzheimer's Disease," Life Sciences 58(15):1201-1207 (1996).

Tariot et al., "Treatment of Alzheimer's Disease: Glimmers of Hope?" Chemistry and Industry 20:801-803, 806-807 (1993).

Tekes et al., "Effect of MAO Inhibitors on the Uptake and Metabolism of Dopamine in Rat and Human Brain," Pol J Pharmacol Pharm. 40(6):653-658 (1988).

Teranishi et al., "Facile Synthesis of 6-Hydroxyindole and 6-Methoxyindole via Regioselective Friedel-Crafts Acylation and Baeyer-Villiger Oxidation," Synthesis 10:1018-1020 (1994).

Terni et al., "Preparation of (aminoalkyl) phenyl morpholinoalkyl carbamates and analogs as C68 cholinesterase inhibitors," WO 96/02524, Feb. 1, 1996, Database CAPLUS on STN®, Chemical abstracts Service (Columbus, Ohio), Accesion No. 1996:340192, abstract.

Thoene et al., "Physicians' Guide to Rare Diseases," Dowden Publishing Company, Inc., Montvale, N.J., pp. 55, 56, 285-288, 215-217, 329-340, 352-355, 359, 361, 395, 396, 456-45440:4396-4405 (1992).

Top et al., "N-Alkylation of Nitriles with Tricarbonylchromium Complexes of Benzyl and Related Alcohols as Synthetic Inteimediates. Further Development of the Ritter Reactions," J. Chem. Soc., Chem. Commun. 224-225 (1979).

Weinstock, "The Pharmacotherapy of Alzheimer's Disease Based on the Cholinergic Hypothesis: an Update," Neurodegeneration 4:349-356 (1995).

White et al., "Mechanism of Monoamine Oxidase-A Inhibition by BW 1370U87," Drug Development Research 25: 191-199 (1992).

Yavich et al., "The interaction of L-deprenyl and scopolamine on spatial learning / memory in rats," Journal of Neural Transmission: Parkinson's Disease and Dementia Section 6(3): 189-197 (1993).

Youdim et al., "Momamine Oxidase," Handbook of Experimental Pharmacology vol. 90/1, Tredelenburg and Weiner, eds., Springer-Verlag, London: Chapter 3, pp. 119-192, 1988.

Zheng et al., "Asymmetric Synthesis of a-Amino Acid Derivatives via an Electrophilic Amination of C76 Chiral Amide Cuprates with Li t-Butyl-N-Tosyloxycarbamate," Tetrahedron Letters 38(16):2817-2820 (1997).

Zhu et al., "Asymmetric Rh-Catalyzed Hydrogenation of Enamides with a Chiral1,4-Bisphosphine Bearing Diphenylphosphino Groups," J. Org. Chem. 63:9590-9593 (1998).

"Agent for Cognition Disorders Acetylcholinesterase Inhibitor," Drugs of the Future 16(1): 16-18 (1991).

"Cognition Enhancer Acetylcholinesterase Inhibitor," E-2020, Drugs of the Future 20(1):77-78 (1995).

"Cognition Enhancer Acetylecholinesterase Inhibitor," TAK-147, Drugs of the Future 20(3):248-250 (1995).

"The Merck Index, an Encyclopedia of Chemicals, Drugs, and Biologicals," Tenth Edition, Windholz et al., eds., Merck & Co. Inc., Rahway, N.J., pp. 149,248-249 (1983).

"The Merck Manual of Diagnosis and Therapy," Fifteenth Edition, vol. 1, Berkow et al., eds., Merck Sharp & Dohme Research Laboratories, Rahway, N.J., pp. 1030-1033 (1987).

"The Merck Manual of Diagnosis and Therapy," Fifteenth Edition, vol. 1, Berkow et al., eds., Merck Sharp & Dohme Research Laboratories, Rahway, N.J., pp. 1054-1055 (1987).

"Effect of Deprenyl on the Progression of Disability in Early Parkinson's Disease," The Parkinson Study Group, The New England Journal of Medicine 321(20):1364 (1989).

"Effects of Tocopherol and Deprenyl on the Progression of Disability in Early Parkinson's Disease," The Parkinson Study Group, The New England Journal of Medicine 328(3): 176-183 (1993).

Japanese patent No. 54132559, Caplus Abstract, Apr. 1978.

U.S. Appl. No. 12/582,491 Requirement for Restriction/Election Jul. 28, 2011.

Petersen, Ronald C. et al., (1999) Mild cognitive impairment. Clinical characterization and outcome. Arch Neurol 56(3):303-308 Erratum: (1999) Arch Neurol 56(6):760.

Handbook of Pharmaceutical Excipients. Published by the Pharmaceutical Press and the American Pharmacist Association. Fourth edition (2003). Edited by Rowe, Raymond C. et al., pp. 188, 430, 449, 705, 725-726, 737-738, 767.

Physician's Desk Reference (2005) 59th edition Publisher: Charles E. Baker, Jr. pp. 1583-1585.

* cited by examiner (a)

(b)

(c)

USE OF LOW-DOSE LADOSTIGIL FOR NEUROPROTECTION

This application claims benefit of U.S. Ser. No. 11/635,922 filed Dec. 8, 2006, U.S. Provisional Application No. 60/792,410, filed Apr. 17, 2006 and U.S. Provisional Application No. 60/748,748, filed Dec. 9, 2005 the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Oxidative stress has been proposed as a pathogenic mechanism in Alzheimer's disease (AD) (P. F. Good et al., *Am. J. Pathol.* (1996) 149:21). Oxidative stress may also contribute to neuronal degeneration and death in disorders ranging from ischemic stroke to Alzheimer's and Parkinson's to age related macular degeneration to amyotrophic lateral sclerosis (M. P. Mattson et al., *J. Neurosci. Res.* (1997) 49:681), disorders in which nitric oxide, via peroxynitrite, plays a key role.

Several strategies for conferring neuroprotection have been developed which target the complex neurochemical processes which follow neuronal malfunction. Older approaches (reviewed by N. G. Wahlgren, in R. Green, "International Review of Neurobiology: Neuroprotective Agents and Cerebral Ischemia", Vol. 40, Academic Press, 1997) including closure of calcium channels (with calcium antagonists), inhibition of glutamate release, and antagonism to NMDA and GABA agonism have not led to any remarkable treatments. With the recent emphasis on the role of reactive oxygen species (ROS) and of the nitrogen oxyanion species, the focus of possible treatments has now shifted to antioxidant and free radical scavengers (K. Hensley et al., in "Neuroinflammation: mechanisms and management" (Ed: P. L. Wood), Humana Press Inc., 1997). R(+)-6-(N-methyl,N-ethyl-carbamoyloxy)-N'-propargyl-1-aminoindan, also known as (3R)-3-(prop-2-ynylamino)-2,3,dihydro-1H-inden-5-yl ethylmethylcarbamate, is disclosed in PCT Application Publication No. WO98/27055 (U.S. Pat. No. 6,303,650, issued Oct. 16, 2001 to Chorev), the entire contents of which are incorporated by reference. This compound has been given the nonproprietary name ladostigil.

Ladostigil has been shown to inhibit acetylcholinesterase (ChE) and monoamine oxidase selectively in the brain (M. Weinstock et al., TV3326, a novel neuroprotective drug with cholinesterase and monoamine oxidase inhibitory activities for the treatment of Alzheimer's disease, *J. Neural Transm. Suppl.* (2000) 60:157-69). As such, ladostigil has been proposed for treatment of depression, Attention Deficit Disorder (ADD), Attention Deficit and Hyperactivity Disorder (ADHD), Tourette's Syndrome, Alzheimer's Disease and other dementias, neurotraumatic disorders and memory disorders in humans (see, e.g., U.S. Pat. No. 6,538,025, issued Mar. 25, 2003 to Chorev et al.). The following dosing of ladostigil has been disclosed: chronic administration of 52 mg/kg to treat comorbidity of dementia with Parkinsonism in a rat model (Y. Sagi, The neurochemical and behavioural effects of the novel cholinesterase-monoamine oxidase inhibitor, ladostigil, in response to L-dopa and L-tryptophan, in rats, Br. J. Pharmacol. (2005) 146(4):553-60); chronic administration of 17 mg/kg to treat hyperanxiety and depressive-like behaviour in a rat model (T. Poltyrev et al., Effect of chronic treatment with ladostigil (TV-3326) on anxiogenic and depressive-like behaviour and on activity of the hypothalamic-pituitary-adrenal axis in male and female prenatally stressed rats, *Psychopharmacology* (2005) 181(1):118-25); and chronic administration of 26 mg/kg to show brain selective MAO inhibition (M. Weinstock, Limited potentiation of blood pressure response to oral tyramine by brain-selective monoamine oxidase A-B inhibitor, TV-3326 in conscious rabbits, Neuropharmacology (2002) 43(6):999-1005, and M. Weinstock, Effect of TV3326, a novel monoamine-oxidase cholinesterase inhibitor, in rat models of anxiety and depression, *Psychopharmacology* (2002) 160(3):318-24, respectively). Ladostigil has also been shown to suppress apoptosis induced by the peroxynitrite-generating agent N-morpholino sydnonimine (Sin-1) in cultured dopaminergic neuroblastoma SH-SY5Y cells (Maruyama et al., Anti-apoptotic action of anti-Alzheimer drug, TV3326 [(N-propargyl)-(3R)-aminoindant-5-yl]-ethyl methyl carbamate, a novel cholinesterase-monoamine oxidase inhibitor, *Neuroscience Letters* (2003) 341:233-236).

MAO inhibitors (MAOIs) are known to have many contraindications, and are associated with high incidences of hypertensive crises (Physician's Desk Reference, 59$^{th}$ Ed. (2005) pgs. 1583-4).

ChE inhibition is known to lower body temperature. (Gordon, 1994) By stimulating muscarinic receptors in the preoptic area of the hypothalamus, heat loss is promoted through peripheral vasodilatation. It has been shown that the fall in body temperature is proportional to the degree of brain ChE inhibition.

Disclosed herein is that ladostigil can be used to reduce the neurodegenerative effects of oxidative nitrative stress at dosage levels that do not cause the noted side effects related to inhibition of monoamine oxidase (MAO) or cholinesterase (ChE).

SUMMARY OF THE INVENTION

The subject invention provides a method of preventing the appearance of symptoms of a neurodegenerative disease in a subject predisposed to the neurodegenerative disease, or of slowing the progression of an early stage neurodegenerative disease to a more advanced stage of the neurodegenerative disease in an afflicted subject, comprising administering to the subject an amount of R(+)-6-(N-methyl,N-ethyl-carbamoyloxy)-N'-propargyl-1-aminoindan or a salt thereof effective to prevent the appearance of symptoms of the disease or to slow the progression of the disease.

The subject invention also provides a method of reducing oxidative stress in the brain of a subject afflicted with oxidative stress, comprising administering to the subject a less than cholinesterase-inhibitory amount or a less than monoamine oxidase-inhibitory amount of R(+)-6-(N-methyl,N-ethyl-carbamoyloxy)-N'-propargyl-1-aminoindan or a salt thereof effective to reduce oxidative stress in the brain of the subject.

The subject invention also provides a method of treating a subject afflicted with mild cognitive impairment comprising administering to the subject an amount of R(+)-6-(N-methyl, N-ethyl-carbamoyloxy)-N'-propargyl-1-aminoindan or a salt thereof effective to treat the subject.

The subject invention also provides a pharmaceutical composition in unit dosage form comprising R(+)-6-(N-methyl, N-ethyl-carbamoyloxy)-N'-propargyl-1-aminoindan in an amount of up to 25 mg, or a corresponding amount of the salt thereof, and a pharmaceutically acceptable carrier.

DETAILED DESCRIPTION

Figure 1:
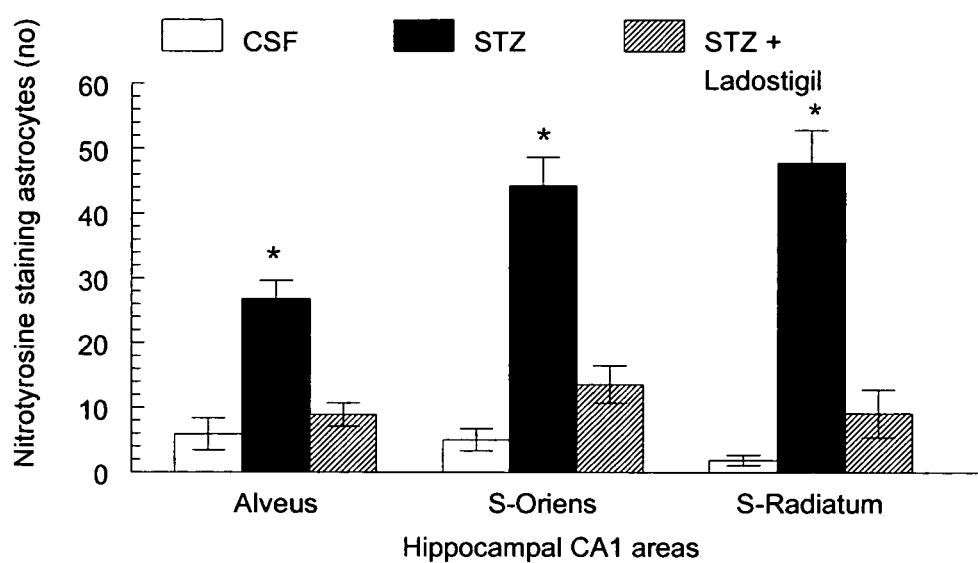
FIG. 1 Effect of ladostigil on nitrotyrosine immunoreactivity in astrocytes of 3 hippocampal regions in the CA1 area one week after a bilateral intracerebroventricular (icv) injection of STZ. An * indicates that the result is significantly different from CSF and STZ+ladostigil, P<0.01.

The subject invention provides a method of preventing the appearance of symptoms of a neurodegenerative disease in a subject predisposed to the neurodegenerative disease, or of slowing the progression of an early stage neurodegenerative disease to a more advanced stage of the neurodegenerative disease in an afflicted subject, comprising administering to the subject an amount of R(+)-6-(N-methyl, N-ethyl-carbamoyloxy)-N'-propargyl-1-aminoindan or a salt thereof effective to prevent the appearance of symptoms of the disease or to slow the progression of the disease.

In an embodiment, the effective amount administered to the subject is a less than cholinesterase-inhibitory amount or a less than monoamine oxidase-inhibitory amount of R(+)-6-(N-methyl, N-ethyl-carbamoyloxy)-N'-propargyl-1-aminoindan or a salt thereof.

In an embodiment, the method comprises administration to the subject a less than cholinesterase-inhibitory amount and a less than monoamine oxidase-inhibitory amount of R(+)-6-(N-methyl,N-ethyl-carbamoyloxy)-N'-propargyl-1-aminoindan or a salt thereof.

In another embodiment, the method comprises administration of a salt of R(+)-6-(N-methyl,N-ethyl-carbamoyloxy)-N'-propargyl-1-aminoindan.

In another embodiment of the method, the salt of R(+)-6-(N-methyl,N-ethyl-carbamoyloxy)-N'-propargyl-1-aminoindan is the tartrate salt.

In yet another embodiment of the method, the administration is acute administration.

In yet another embodiment of the method, the subject is a human.

In yet another embodiment of the method with acute administration to humans, the less than monoamine oxidase-inhibitory amount of R(+)-6-(N-methyl,N-ethyl-carbamoyloxy)-N'-propargyl-1-aminoindan is no more than 1.7 mg/kg/day of the subject, or a corresponding amount of the salt thereof.

In yet another embodiment of the method with acute administration to humans, the salt is the tartrate salt and the corresponding amount of the salt is no more than 2.1 mg/kg/day of the subject.

In yet another embodiment of the method with acute administration to humans, the less than cholinesterase-inhibitory amount of R(+)-6-(N-methyl,N-ethyl-carbamoyloxy)-N'-propargyl-1-aminoindan is no more than 2.3 mg/kg/day of the subject, or a corresponding amount of the salt thereof.

In yet another embodiment of the method with acute administration to humans, the salt is the tartrate salt and the corresponding amount of the salt is no more than 2.9 mg/kg/day of the subject.

In a further embodiment of the method, the administration is chronic administration.

In a further embodiment of the method, the subject is a human.

In yet a further embodiment of the method with humans, the amount of R(+)-6-(N-methyl,N-ethyl-carbamoyloxy)-N'-propargyl-1-aminoindan is no more than 0.37 mg/kg/day of the subject, or a corresponding amount of the salt thereof.

In yet a further embodiment of the method with to humans, the salt is the tartrate salt and the corresponding amount of the salt is no more than 0.46 mg/kg/day of the subject.

In yet a further embodiment of the method with to humans, the amount of R(+)-6-(N-methyl,N-ethyl-carbamoyloxy)-N'-propargyl-1-aminoindan is no more than 2.3 mg/kg/day of the subject, or a corresponding amount of the salt thereof.

In yet a further embodiment of the method with to humans, the salt is the tartrate salt and the corresponding amount of the salt is no more than 2.9 mg/kg/day of the subject.

In another embodiment of the method, the amount of R(+)-6-(N-methyl,N-ethyl-carbamoyloxy)-N'-propargyl-1-aminoindan or a salt thereof administered is 10 mg/day-25 mg/day of the subject.

By 10 mg/day-25 mg/day it is meant that all hundredth, tenth and integer unit amounts within the range are specifically disclosed as part of the invention. Thus, 10.01, 10.02 . . . 24.99; 10.1, 10.2 . . . 24.9; and 11, 12 . . . 24 mg/day unit amounts are included as embodiments of this invention.

In another embodiment of the method, the amount of R(+)-6-(N-methyl,N-ethyl-carbamoyloxy)-N'-propargyl-1-aminoindan or a salt thereof administered is 0.14 mg/kg/day-0.42 mg/kg/day of the subject.

By 0.14 mg/kg/day-0.42 mg/kg/day it is meant that all hundredth and tenth unit amounts within the range are specifically disclosed as part of the invention. Thus, 0.15, 0.16, 0.17 . . . 0.41 mg/kg/day unit amounts are included as embodiments of this invention.

In another embodiment of the method, the amount of R(+)-6-(N-methyl,N-ethyl-carbamoyloxy)-N'-propargyl-1-aminoindan or a salt thereof administered is 0.15 mg/day of the subject.

In another embodiment of the method, the amount of R(+)-6-(N-methyl, N-ethyl-carbamoyloxy)-N'-propargyl-1-aminoindan or a salt thereof administered is 0.5 mg/kg of the subject, 0.784 mg/kg of the subject, 1 mg/kg of the subject, 1.5 mg/kg of the subject, 2 mg/kg of the subject, 3 mg/kg of the subject or 4 mg/kg of the subject.

In another embodiment, the method further comprises administering to the subject an antioxidant.

In another embodiment of the method, the neurodegenerative disease is Alzheimer's disease, dementia, mild cognitive impairment, Parkinson's disease, age-related macular degeneration, or amyotrophic lateral sclerosis.

In an embodiment of the method to treat dementia, the dementias include static dementia, senile dementia, presenile dementia, progressive dementia, vascular dementia or Lewy body dementia.

In an embodiment, the method slows the progression of an early stage neurodegenerative disease to a more advanced stage of the neurodegenerative disease in the subject.

In an embodiment, the method prevents the appearance of symptoms of a neurodegenerative disease in a subject predisposed to the disease.

The subject invention also provides a method of treating a subject afflicted with a neurodegenerative disease, comprising administering to the subject a less than cholinesterase-inhibitory amount or a less than monoamine oxidase-inhibitory amount of R(+)-6-(N-methyl, N-ethyl-carbamoyloxy)-N'-propargyl-1-aminoindan or a salt thereof effective to treat the subject.

In an embodiment, the method comprises administering to the subject a less than cholinesterase-inhibitory amount and less than monoamine oxidase-inhibitory amount of R(+)-6-(N-methyl, N-ethyl-carbamoyloxy)-N'-propargyl-1-aminoindan or a salt thereof effective to treat the subject.

In another embodiment, the method comprises administration of a salt of R(+)-6-(N-methyl, N-ethyl-carbamoyloxy)-N'-propargyl-1-aminoindan. The salt of R(+)-6-(N-methyl, N-ethyl-carbamoyloxy)-N'-propargyl-1-aminoindan may be the tartrate salt.

In a further embodiment of the method, the subject is a human.

In yet a further embodiment of the method with humans, the less than monoamine oxidase-inhibitory amount of R(+)-6-(N-methyl, N-ethyl-carbamoyloxy)-N'-propargyl-1-aminoindan is no more than 0.37 mg/kg/day of the subject, or a corresponding amount of the salt thereof.

In yet a further embodiment of the method with humans, the salt is the tartrate salt and the corresponding amount of the salt is no more than 0.46 mg/kg/day of the subject.

In yet a further embodiment of the method with humans, the less than cholinesterase-inhibitory amount of R(+)-6-(N-methyl,N-ethyl-carbamoyloxy)-N'-propargyl-1-aminoindan is no more than 2.3 mg/kg/day of the subject, or a corresponding amount of the salt thereof.

In yet a further embodiment of the method with humans, wherein the salt is the tartrate salt and the corresponding amount of the salt is no more than 2.9 mg/kg/day of the subject. Other amounts disclosed herein can also be used in this method.

In another embodiment of the method, the amount of R(+)-6-(N-methyl,N-ethyl-carbamoyloxy)-N'-propargyl-1-aminoindan or a salt thereof administered is 10 mg/day-25 mg/day of the subject.

By 10 mg/day-25 mg/day it is meant that all hundredth, tenth and integer unit amounts within the range are specifically disclosed as part of the invention. Thus, 10.01, 10.02 ... 24.99; 10.1, 10.2 ... 24.9; and 11, 12 ... 24 mg/day unit amounts are included as embodiments of this invention.

In another embodiment of the method, the amount of R(+)-6-(N-methyl,N-ethyl-carbamoyloxy)-N'-propargyl-1-aminoindan or a salt thereof is 0.5 mg/kg of the subject, 0.784 mg/kg of the subject, 1 mg/kg of the subject, 1.5 mg/kg of the subject, 2 mg/kg of the subject, 3 mg/kg of the subject or 4 mg/kg of the subject.

In another embodiment of the method, the neurodegenerative disease is Alzheimer's disease, dementia, mild cognitive impairment, Parkinson's disease, age-related macular degeneration, or amyotrophic lateral sclerosis.

In another embodiment of the method, dementias include static dementia, senile dementia, presenile dementia, progressive dementia, vascular dementia or Lewy body dementia.

In another embodiment of the method, dementias include static dementia, senile dementia, presenile dementia, progressive dementia or vascular dementia.

The subject invention also provides a method of reducing oxidative stress in the brain of a subject afflicted with oxidative stress, comprising administering to the subject a less than cholinesterase-inhibitory amount or a less than monoamine oxidase-inhibitory amount of R(+)-6-(N-methyl,N-ethyl-carbamoyloxy)-N'-propargyl-1-aminoindan or a salt thereof effective to reduce oxidative stress in the brain of the subject.

In an embodiment, the method comprises administering to the subject a less than cholinesterase-inhibitory amount and a less than monoamine oxidase-inhibitory amount of R(+)-6-(N-methyl,N-ethyl-carbamoyloxy)-N'-propargyl-1-aminoindan or a salt thereof effective to treat the subject.

In another embodiment, the method comprises administration of a salt of R(+)-6-(N-methyl,N-ethyl-carbamoyloxy)-N'-propargyl-1-aminoindan.

In another embodiment of the method, the salt of R(+)-6-(N-methyl,N-ethyl-carbamoyloxy)-N'-propargyl-1-aminoindan is the tartrate salt.

In yet another embodiment of the method, the administration is acute administration.

In yet another embodiment of the method, subject is a human.

In yet another embodiment of the method with acute administration to humans, the less than monoamine oxidase-inhibitory amount of R(+)-6-(N-methyl,N-ethyl-carbamoyloxy)-N'-propargyl-1-aminoindan is no more than 1.7 mg/kg/day of the subject, or a corresponding amount of the salt thereof.

In yet another embodiment of the method with acute administration to humans, the salt is the tartrate salt and the corresponding amount of the salt is no more than 2.1 mg/kg/day of the subject.

In yet another embodiment of the method with acute administration to humans, the less than cholinesterase-inhibitory amount of R(+)-6-(N-methyl,N-ethyl-carbamoyloxy)-N'-propargyl-1-aminoindan is no more than 2.3 mg/kg/day of the subject, or a corresponding amount of the salt thereof.

In yet another embodiment of the method with acute administration to humans, the salt is the tartrate salt and the corresponding amount of the salt is no more than 2.9 mg/kg/day of the subject.

In a further embodiment of the method, the administration is chronic administration.

In a further embodiment of the method, the subject is a human.

In yet a further embodiment of the method with chronic administration to humans, the less than monoamine oxidase-inhibitory amount of R(+)-6-(N-methyl,N-ethyl-carbamoyloxy)-N'-propargyl-1-aminoindan is no more than 0.37 mg/kg/day of the subject, or a corresponding amount of the salt thereof.

In yet a further embodiment of the method with chronic administration to humans, the salt is the tartrate salt and the corresponding amount of the salt is no more than 0.46 mg/kg/day of the subject.

In yet a further embodiment of the method with chronic administration to humans, the less than cholinesterase-inhibitory amount of R(+)-6-(N-methyl,N-ethyl-carbamoyloxy)-N'-propargyl-1-aminoindan is no more than 2.3 mg/kg/day of the subject, or a corresponding amount of the salt thereof.

In yet a further embodiment of the method with chronic administration to humans, the salt is the tartrate salt and the corresponding amount of the salt is no more than 2.9 mg/kg/day of the subject.

In another embodiment of the method, the amount of R(+)-6-(N-methyl,N-ethyl-carbamoyloxy)-N'-propargyl-1-aminoindan or a salt thereof administered is 10 mg/day-25 mg/day of the subject.

By 10 mg/day-25 mg/day it is meant that all hundredth, tenth and integer unit amounts within the range are specifically disclosed as part of the invention. Thus, 10.01, 10.02 . . . 24.99; 10.1, 10.2 . . . 24.9; and 11, 12 . . . 24 mg/day unit amounts are included as embodiments of this invention.

In another embodiment of the method, the amount of R(+)-6-(N-methyl,N-ethyl-carbamoyloxy)-N'-propargyl-1-aminoindan or a salt thereof effective to treat the subject is 0.5 mg/kg of the subject, 0.784 mg/kg of the subject, 1 mg/kg of the subject, 1.5 mg/kg of the subject, 2 mg/kg of the subject, 3 mg/kg of the subject or 4 mg/kg of the subject.

In another embodiment of the method, the oxidative stress occurs in the hippocampus region of the brain.

In another embodiment of the method, the oxidative stress occurs in the astrocytes of the hippocampus region of the brain.

The subject invention also provides a method of treating a subject afflicted with mild cognitive impairment comprising administering to the subject an amount of R(+)-6-(N-methyl,N-ethyl-carbamoyloxy)-N'-propargyl-1-aminoindan or a salt thereof effective to treat the subject.

The subject invention also provides a method of treating a subject afflicted with mild cognitive impairment comprising administering to the subject a less than cholinesterase-inhibitory amount or a less than monoamine oxidase-inhibitory amount of R(+)-6-(N-methyl,N-ethyl-carbamoyloxy)-N'-propargyl-1-aminoindan or a salt thereof effective to treat the subject.

In an embodiment of the method, the less than cholinesterase-inhibitory amount or the less than monoamine oxidase-inhibitory amount of R(+)-6-(N-methyl,N-ethyl-carbamoyloxy)-N'-propargyl-1-aminoindan or the salt thereof is effective to delay the progress of MCI to Alzheimer's disease.

In another embodiment, the method comprises administering to the subject a less than cholinesterase-inhibitory amount and less than monoamine oxidase-inhibitory amount of R(+)-6-(N-methyl,N-ethyl-carbamoyloxy)-N'-propargyl-1-aminoindan or a salt thereof effective to treat the subject.

In another embodiment, the method comprises administration of a salt of R(+)-6-(N-methyl,N-ethyl-carbamoyloxy)-N'-propargyl-1-aminoindan.

In another embodiment of the method, the salt of R(+)-6-(N-methyl,N-ethyl-carbamoyloxy)-N'-propargyl-1-aminoindan is the tartrate salt.

In a further embodiment of the method, the subject is a human.

In yet a further embodiment of the method with humans, the amount of R(+)-6-(N-methyl,N-ethyl-carbamoyloxy)-N'-propargyl-1-aminoindan is no more than 0.37 mg/kg/day of the subject, or a corresponding amount of the salt thereof.

In yet a further embodiment of the method with humans, the salt is the tartrate salt and the corresponding amount of the salt is no more than 0.46 mg/kg/day of the subject.

In yet a further embodiment of the method with humans, the amount of R(+)-6-(N-methyl,N-ethyl-carbamoyloxy)-N'-propargyl-1-aminoindan is no more than 2.3 mg/kg/day of the subject, or a corresponding amount of the salt thereof.

In yet a further embodiment of the method with to humans, wherein the salt is the tartrate salt and the corresponding amount of the salt is no more than 2.9 mg/kg/day of the subject.

In another embodiment of the method, the amount of R(+)-6-(N-methyl,N-ethyl-carbamoyloxy)-N'-propargyl-1-aminoindan or a salt thereof administered is 10 mg/day-25 mg/day of the subject.

By 10 mg/day-25 mg/day it is meant that all hundredth, tenth and integer unit amounts within the range are specifically disclosed as part of the invention. Thus, 10.01, 10.02 . . . 24.99; 10.1, 10.2 . . . 24.9; and 11, 12 . . . 24 mg/day unit amounts are included as embodiments of this invention.

In another embodiment of the method, the amount of R(+)-6-(N-methyl,N-ethyl-carbamoyloxy)-N'-propargyl-1-aminoindan or a salt thereof is 0.5 mg/kg of the subject, 0.784 mg/kg of the subject, 1 mg/kg of the subject, 1.5 mg/kg of the subject, 2 mg/kg of the subject, 3 mg/kg of the subject or 4 mg/kg of the subject.

The subject invention also provides a pharmaceutical composition in unit dosage form comprising R(+)-6-(N-methyl,N-ethyl-carbamoyloxy)-N'-propargyl-1-aminoindan in an amount of up to 25 mg, or a corresponding amount of a pharmaceutically acceptable salt thereof, and a pharmaceutically acceptable carrier.

In an embodiment, the method comprises R(+)-6-(N-methyl,N-ethyl-carbamoyloxy)-N'-propargyl-1-aminoindan in an amount of 10 mg-25 mg or a corresponding amount of a pharmaceutically acceptable salt thereof, and a pharmaceutically acceptable carrier.

In a further embodiment of the method, the pharmaceutically acceptable salt is the tartrate salt.

This invention also provides a use of an amount of R(+)-6-(N-methyl,N-ethyl-carbamoyloxy)-N'-propargyl-1-aminoindan or a salt thereof in the manufacture of a medicament for preventing the appearance of symptoms of a neurodegenerative disease in a subject predisposed to the neurodegenerative disease or for slowing the progression of an early stage neurodegenerative disease to a more advanced stage of the neurodegenerative disease. The amount of R(+)-6-(N-methyl,N-ethyl-carbamoyloxy)-N'-propargyl-1-aminoindan or salt thereof in the medicament is effective to prevent the appearance of symptoms of the disease or to slow the progression of the disease. The amount of R(+)-6-(N-methyl,N-ethyl-carbamoyloxy)-N'-propargyl-1-aminoindan or salt thereof may also be a less than cholinesterase-inhibitory amount or a less than monoamine oxidase-inhibitory amount. Other embodiments disclosed herein may also be implemented in the context of this use.

This invention further provides a use of an amount of R(+)-6-(N-methyl,N-ethyl-carbamoyloxy)-N'-propargyl-1-aminoindan or a salt thereof in the manufacture of a medicament for reducing oxidative stress in the brain of a subject afflicted with such oxidative stress. Other embodiments disclosed herein including the amounts of R(+)-6-(N-methyl,N-ethyl-carbamoyloxy)-N'-propargyl-1-aminoindan or salt thereof in the medicament may be readily implemented in the context of this use.

This invention additionally provides a use of an amount of R(+)-6-(N-methyl,N-ethyl-carbamoyloxy)-N'-propargyl-1-aminoindan or a salt thereof for manufacturing a medicament for treating mild cognitive impairment in a subject afflicted therewith. Other embodiments disclosed herein including the amount of R(+)-6-(N-methyl,N-ethyl-carbamoyloxy)-N'-propargyl-1-aminoindan or salt thereof in the medicament may be readily implemented in the context of this use.

The compound R(+)-6-(N-methyl,N-ethyl-carbamoyloxy)-N'-propargyl-1-aminoindan may be prepared as pharmaceutical compositions particularly useful for the prevention or treatment of neurodegenerative diseases or of oxidative stress. For example, the compositions can also contain adjunct therapy agents for the neurodegenerative disease or additional antioxidants.

Such compositions may comprise ladostigil or pharmaceutically acceptable salts thereof, together with pharmaceutically acceptable carriers and/or excipients. Dosages of unit dosage forms may be in the range of, e.g., 1-25 mg, or preferably 5-20 mg. In the practice of this invention, pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

Specific examples of pharmaceutical acceptable carriers and excipients that may be used to formulate oral dosage forms of the present invention are described, e.g., in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

As used herein, a "pharmaceutically acceptable" carrier is one that is suitable for administration to humans and/or animals without undue adverse side effects (such as toxicity, irritation, and allergic response) commensurate with a reasonable benefit/risk ratio.

As used herein, a "neurodegenerative disease" refers to a disease in which degeneration occurs in either gray or white matter, or both, of the nervous system. Thus, such a disease can be diabetic neuropathy, senile dementias, Alzheimer's disease, Mild Cognitive Impairment (MCI), Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease and lipoproteinemia.

As used herein, "predisposed" to a neurodegenerative disease or to oxidative stress in the brain may refer to a genetic, familial or chemically-induced predisposition.

As used herein, a "less than monoamine-oxidase inhibitory amount" refers to an amount that causes no more than 25% MAO inhibition upon acute administration to a subject, or no more than 30% MAO inhibition during chronic administration to a subject.

A "less than cholinesterase-inhibitory amount" refers to an amount that causes no more than 30% ChE inhibition upon acute administration to a subject, or no more than 30% ChE inhibition during chronic administration to a subject.

In the methods described, the administration may be periodic or regular. Thus, the administration may be in a single unit dose of the desired amount per a given period, e.g. once per day, week, month, etc, or it may be composed of multiple dosages adding up to the desired amount over the period. For example, administration may be once, twice, three or four times every day, or every 5 days, every week, 2 weeks, 3 weeks, month, 2 months, 3 months, 6 months or year.

As used herein, "acute" administration refers to a single administration to a subject.

As used herein, "chronic" administration refers to more than one administration to a subject, each administration occurring before the previous is completely cleared from the subject. In an embodiment, chronic administration may be administration seven consecutive times at regular intervals, e.g., daily.

As used herein, a subject "afflicted" with neurodegenerative disease or with oxidative stress in the brain means the subject has been diagnosed with neurodegenerative disease or oxidative stress in the brain.

Thus, this invention provides a method for delaying or preventing development of, or appearance of symptoms of, a neurodegenerative disease in a subject predisposed to such disease, as well as a method for slowing or suppressing progression of such a disease in a subject afflicted with an early stage of such disease.

EXPERIMENTAL DETAILS

Monoamine Oxidase (MAO) Inhibition Assay

The level of MAO (MAO-A and MAO-B) inhibition can be determined by routine methods, including those detailed below.

In Vivo

Rats and mice are treated by subcutaneous (s.c.) or intraperitoneal (i.p.) injection or oral (p.o.) administration of the compound to be tested. Animals are decapitated approximately 2 hours after drug treatment and MAO activity is determined in the brain, intestine, and/or liver. MAO activity is expressed as percentage of enzyme activity relative to a control group administered with vehicle only. Effective doses producing 50% MAO inhibition ($ED_{50}$ values) are calculated from inhibition curves.

Repeated treatment by ladostigil (e.g. daily doses for 7 days) can be used to calculate inhibition achieved through chronic administration.

In the case of ladostigil tartrate, this method was used to determine that amounts up to 20.4 mg/kg of ladostigil base (acute administration) and up to 4.5 mg/kg of ladostigil base (chronic administration) cause no more than 25% MAO inhibition (both MAO-A and MAO-B).

In Vitro

The MAO enzyme obtained from a homogenate of rat brain in 0.3M sucrose, which was centrifuged at 600 g for 15 minutes. The supernatant is diluted appropriately in 0.05M phosphate buffer, and pre-incubated with serial dilutions of test compounds for 20 minutes at 37° C. $^{14}C$-Labeled substrates (2-phenylethylamine, hereinafter PEA; 5-hydroxytryptamine, hereinafter 5-HT) are then added, and the incubation continued for a further 20 minutes (PEA), or 30-45 minutes (5-HT). Substrate concentrations used are 50 μM (PEA) and 1 mM (5-HT). In the case of PEA, enzyme concentration is chosen so that not more than 10% of the substrate is metabolized during the course of the reaction. Deaminated products are extracted into toluene-ethyl acetate (1:1 v/v) containing 0.6% (w/v) 2,5-diphenyloxazole (ppo) prior to determination by liquid scintillation counting. Radioactivity in the eluate indicates the production of neutral and acidic metabolites formed as a result of MAO activity. Activity of MAO in the sample is expressed as a percentage of control activity in the absence of inhibitors after subtraction of appropriate blank values. The activity determined using PEA as substrate is referred to as MAO-B, and that determined using 5-HT as MAO-A.

Concentrations of inhibitor producing 50% inhibition of substrate metabolism ($IC_{50}$) are calculated from the inhibition curves.

Acetylcholinesterase (ChE) Inhibition Assay

The level of ChE inhibition can be determined by routine methods, including those detailed below.

In Vivo

In vivo measurement of ChE inhibition is similar to that of in vivo measurement of MAO inhibition, except that cynomolgus monkeys are treated, and tissues are examined for brain, plasma and erythrocytes ChE inhibition.

In the case of ladostigil tartrate, this method was used to determine that amounts up to 7.0 mg/kg ladostigil base (acute or chronic administration) cause no more than 30% inhibition.

In Vitro

Human erythrocyte acetylcholinesterase (type XIII, Sigma Israel), is prepared in a stock solution of 1 U/ml, containing Triton (1%) and bovine serum albumin (0.05%) in phosphate buffer (pH 8). The enzyme (0.05 U) is incubated with 3-5 different concentrations of test compound (in triplicate) for periods of from 15 to 60 minutes at 37° C. The substrate acetylthiocholine (0.075M) and 5,5'-dithiobis-(2-nitrobenzoic acid) (DTNB, 0.01M) are then added and the rate of hydrolysis of the substrate which yields a yellow product monitored spectrophotomerically at 412 nM (Ellman et al., Biochem Pharmacol. (1961) 7: 88-95). The percentage inhibition of ChE by each concentration of drug is calculated by comparison with that of enzyme in the absence of drug. The concentration of each drug that inhibits ChE by 50% ($IC_{50}$) at the time of peak activity is then calculated.

A standard method for converting a dosage used in animals to a dosage appropriate for human use is publicly available (Guidance for Industry: Estimating the Maximum Safe Starting Dose in Initial Clinical Trials for Therapeutics in Adult Healthy Volunteers, U.S. Dept. HHS/FDA/CDER (July 2005), at http://www.fda.gov/cder/guidance/5541fnl.doc). The dose conversion is species dependent. Interspecies dose conversion consists of dividing the animal dosage by a standard factor in order to derive the dosage for human use. The recommended standard factor for converting to the human equivalent dose for an average 60 kg human based on the animal species is, e.g., 12.3 for mice, 6.2 for rats, 3.1 for cynomolgous monkeys. Alternatively, the human equivalent dose (HED) can be obtained using the following formula: HED=animal dose in mg/kg * (animal weight in kg/human weight in kg)^0.33.

Animal Testing

Streptozotocin ("STZ") is known to cause oxidative stress in pancreatic beta cells when injected parenterally (Takasu et al., Streptozotocin- and alloxan-induced $H_2O_2$ generation and DNA fragmentation in pancreatic islets, Diabetes (1991) 40:1141-5). Previous studies by the inventors have shown that a single bilateral icv injection of STZ causes impairment of episodic memory as measured by the object recognition test 2 weeks later, which is still present after 8 weeks. Memory deficits are seen 3-8 weeks later, particularly after 3 icv injections of STZ (Lannert and Hoyer, 1998) and can be reduced by chronic treatment with antioxidants, melatonin and resveratrol (Sharma and Gupta, 2001, 2002), supporting a role of ROS in their aetiology.

Previous studies by the inventors have also shown that STZ induces oxidative nitrative stress in the stratum oriens of the hippocampus after one week, and that a single STZ injection reduces the levels of low molecular weight antioxidants in the fornix and corpus callosum. In a detailed histological examination of the brain after intracerebroventricular (icv) injection of streptozotocin (STZ) in rats it was found that microglial activation occurs in discrete areas (Shoham et al., 2003).

Icv STZ causes activation of astrocytes and microglia in the hippocampus and at the site of STZ injection, which leads to the production of nitric oxide (NO) and ultimately reactive oxygen species ($O_2$— and OH—) (Simmons et al., Induction of nitric oxide synthase in glial cells, J. Neurochem. (1992) 59:897-905).

Activated astrocytes express excitatory amino acid receptors, take up glutamate, and are also at risk of oxidative stress (Ouyang and Giffard, 2004). Thus, a common origin of oxidative stress in hippocampus could be excess excitatory stimulation (glutamate-GABA imbalance) that involves intracellular calcium dysregulation that can lead to disruption of intracellular anti-oxidant defense systems (Lipton et al., Excitatory amino acids as a final common pathway for neurological disorders, N. Engl. J. Med. (1994) 330:613-22).

Activation followed by a loss of astroglia can result in dysregulation of glia to neuron signaling leading (Kielian et al., Effects of neuroinflammation on glia-glia gap junctional intercellular communication: a perspective, Neurochem. Int. (2004) 45:429-36). This may induce a memory deficit by slowing impulse conduction in myelinated neurons in the cortex and hippocampus and eventually lead to a reduction in hippocampal cholinergic transmission.

Thus, STZ-induced oxidative stress was selected as a model to test the anti-oxidant potential of ladostigil.

Example 1

The study was performed on male Sprague-Dawley rats (Harlan, Jerusalem) weighing 320-340 g, aged 4 months, according to the guidelines of the University Committee for Institutional Animal Care and based on those of the National Institutes of Health, USA. The rats were housed for one week prior to surgery in the Animal House at an ambient temperature of 21±1° C. and a 12 hr diurnal light cycle (lights on at 0700 hr).

Male Sprague-Dawley rats (30) weighing 320-340 g, were anaesthetized by an intraperitoneal (i.p.) injection of Equithesin 0.3 ml/kg. STZ (0.5 mg) in 2 µl artificial cerebrospinal fluid (CSF) was injected into each lateral ventricle of 20 rats. The stereotaxic co-ordinates for icv injection were: 0.9 mm posterior, 1.8 mm lateral and 3.8 mm ventral from the bregma level. Control rats (10) received a bilateral injection of 2 µl artificial CSF. Half of the STZ-injected rats were given ladostigil (1 mg/kg) orally in a volume of (1 ml/kg) one week before, and for one week after icv STZ. The remainder, received 1 ml/kg water. The rats were anaesthetized with sodium pentobarbitone, perfused transcardially and the brains processed for immunocytochemistry as described below.

Histopathology

The brains were sectioned in a cryostat in 30 µm thick slices and stained immunochemically with the following markers: Nitrotyrosine, a marker of nitrative/oxidative stress, was stained with rabbit anti-nitrotyrosine from Upstate (Lake Placid, N.Y., USA), diluted 1:100. Glial fibrillary acidic protein (GFAP), a marker of astrocyte activation, was stained with mouse antibody, clone GA-5 from Sigma (Rehovot, Israel), diluted 1:500. 1:250. For rabbit antibodies, the secondary donkey anti-rabbit conjugated with horseradish peroxidase from Chemicon (Temecula, Calif., USA), was diluted 1:200. For mouse anti-GFAP, the secondary goat anti mouse conjugated with horseradish peroxidase from Sigma (Rehovot, Israel), was diluted 1:100. Colour development was obtained by reaction with diaminobenzidine and hydrogen peroxide as described in Shoham et al., Intracerebroventricular injection of streptozotocin causes neurotoxicity to myelin that contributes to spatial memory deficits in rats, Exp. Neurol. (2003) 184:1043-52. Images were obtained by bright field microscopy and quantitative assessments of appropriate markers were made by means of densitometric measurements with AnalySIS software.

Confocal Microscopy for Correlation Between Astrocyte Activation and Oxidative Stress Brain sections were incubated with both rabbit anti NT and mouse anti GFAP. Instead of the DAB-peroxidase color reaction, the secondary antibodies were conjugated with fluorescein isothiocyanate (FITC) (NT) or with rhodamine isothiocyanate (RITC) (GFAP).

Quantification with Image Analysis

NT-immunoreactive astrocytes were seen in the stratum oriens, stratum, radiatum and alveus of the hippocampus. Rectangular fields measuring 200 µm×100 µm were sampled from these areas in two sections containing the hippocampus from each rat. The percentage area in which nitrotyrosine immunoreactivity was seen was computed and averaged between the two sections.

Statistical Analysis

Densitometic data were analyzed by univariate ANOVA followed by Duncan's post hoc test.

TABLE 1*

| Rat | Treatment | Nitrotyrosine Immunoreactivity | | |
|---|---|---|---|---|
| | | Alveus | Stratum oriens | Stratum radiatum |
| C1 | CSF n = 6 | 0 | 0 | 0 |
| C2 | | 14.5 | 5.5 | 4 |
| C3 | | 2.5 | 5 | 5 |
| C4 | | 12 | 7 | 1.5 |
| C5 | | 6.5 | 11.5 | 0.5 |
| C6 | | 0 | 1 | 0.5 |
| | Mean ± SEM | 5.9 ± 2.5 | 5.0 ± 1.7 | 1.9 ± 0.8 |
| S1 | STZ n = 7 | 30 | 40 | 46 |
| S2 | | 33.5 | 60 | 48 |
| S3 | | 22 | 33 | 52 |
| S4 | | 23.5 | 55.5 | 69.5 |
| S5 | | 20 | 43 | 40.5 |
| S6 | | 20 | 28 | 25.5 |
| S7 | | 38.5 | 50.5 | 53 |
| | Mean ± SEM | 26.8 ± 2.8 | 44.3 ± 4.4 | 47.8 ± 5.0 |
| SL1 | STZ + ladostigil n = 5 | 4 | 14.5 | 1.5 |
| SL2 | | 9.5 | 19 | 22 |
| SL3 | | 7 | 5.5 | 3 |
| SL4 | | 9 | 8.5 | 7.5 |
| SL5 | | 15 | 20.5 | 11.5 |
| | Mean ± SEM | 8.9 ± 1.8 | 13.6 ± 2.9 | 9.1 ± 3.7 |

*Data represent mean of two sections per rat

One week after a single icv injection of STZ a significant increase in nitrotyrosine staining was seen in the stratum oriens, alveus and stratum radiatum of the hippocampal CA1 field. Confocal microscopy revealed that the nitrotyrosine immunoreactivity occurred in reactive astrocytes. Ladostigil completely prevented the increase in nitrotyrosine immunoreactivity in astrocytes in three areas of the CA1 region of the hippocampus (FIG. 1).

Discussion

A single bilateral icv injection of streptozotocin ("STZ") induces oxidative nitrative stress in the stratum oriens of the hippocampus after one week. The present invention extends this finding to two adjacent areas in the CA1 region of the hippocampus, the alveus and stratum. The induction of nitrotyrosine immunoreactivity suggests a unique vulnerability of this region to some STZ-induced processes that involve oxidative stress. Specifically, STZ causes activation followed by a loss of astrocytes in this brain region, thereby increasing the likelihood of glutamate overactivity.

Daily oral administration of ladostigil (1.0 mg/kg), from one week before, to one week after icv STZ injection prevented the increase in nitrotyrosine immunoreactivity in astrocytes in 3 hippocampal fields. This suggests that a low dose of ladostigil can reduce oxidative-nitrative stress in astrocytes in a defined hippocampal region, which may lessen the reduction in signaling in hippocampal pyramidal cells by STZ thereby reducing the memory deficit.

Example 2

The study was performed on male Sprague-Dawley rats (Harlan, Jerusalem) weighing 320-340 g, aged 4 months, according to the guidelines of the University Committee for Institutional Animal Care and based on those of the National Institutes of Health, USA. The rats were housed for one week prior to surgery in the Animal House at an ambient temperature of 21±1° C. and a 12 hr diurnal light cycle (lights on at 0700 hr).

Male Sprague-Dawley rats (63) weighing 320-340 g, aged 4 months, were anesthetized by an intraperitoneal injection of Equithesin 0.3 ml/kg. STZ (0.5 mg) dissolved in 2 µl artificial cerebrospinal fluid (CSF) was injected into each lateral ventricle of 45 rats. The stereotaxic co-ordinates for icv injection were: 0.9 mm posterior, 1.8 mm lateral and 3.8 mm ventral from the bregma level. Control rats (18) received a bilateral injection of 2 µl artificial CSF. STZ-injected rats (25) were given ladostigil (1 mg/kg of the hemitartrate salt/day) orally in a volume of (1 ml/kg) from one week before, until 1 or 8 weeks after icv STZ. The remaining 20 rats received 1 ml/kg water. The rats were housed two per cage with free access to food and water until the behavioral, enzymatic and cytochemical measurements were completed.

Immunohistochemistry

One week after icv injection, 8 rats injected with icv CSF, 7 rats given STZ alone, and 7 treated with ladostigil were anesthetized with sodium pentobarbitone, perfused transcardially and the brains processed for immunocytochemistry. This procedure was repeated in another 6 rats of each group, 8 weeks after icv injection, when the rats had been tested for memory deficits as described below. Floating sections 30 µm thick were prepared from the brains in a cryostat and were cryopreserved as described in Shoham et al., supra.

Glial Activation and Nitrative Stress

Nitrotyrosine, (NT) a marker of nitrative/oxidative stress, was stained with rabbit anti-nitrotyrosine from Upstate (Lake Placid, N.Y., USA), diluted 1:100 followed by the secondary donkey anti-rabbit conjugated with horseradish peroxidase from Chemicon (Temecula, Calif., USA), was diluted 1:200. GFAP, a marker of astrocyte activation, was stained first with mouse antibody, clone GA-5 from Sigma (Rehovot, Israel), diluted 1:500 then with the secondary goat anti-mouse conjugated with horseradish peroxidase from Sigma (Rehovot, Israel), diluted 1:100. Microglia were stained by incubation with biotinylated lectin (Griffonia Bandeirea Simplicifolia, Vector laboratories, Burlingame Calif.), followed by extravidin conjugation with horseradish peroxidase. Color was developed by reaction with diaminobenzidine and hydrogen peroxide as previously described in Shoham et al., supra. Images were obtained by bright field microscopy and quantitative assessments of appropriate markers were made using AnalySIS software.

Cholinergic Markers

Cholinergic neurons were stained for choline acetyl transferase (ChAT) with goat anti ChAT 1:200, (Chemicon, Temecula, Calif., USA), vesicular acetylcholine transporter (VAChT) with rabbit anti VAChT (Sigma, Rehovot, Israel) 1:100, and for nerve growth factor receptor (NGFR) rabbit anti NGFR (Alomone labs, Jerusalem, Israel) 1:100. The secondary antibody solutions were donkey anti goat and donkey anti rabbit 1:200, each conjugated with horseradish peroxidase (Chemicon, Temecula, Calif., USA). The final color reaction was developed as previously described in Shoham et al., supra.

Confocal Microscopy

To detect evidence of oxidative-nitrative stress in activated astrocytes, brain sections were incubated with both rabbit anti NT and mouse anti GFAP. Instead of the DAB-peroxidase color reaction, the secondary antibodies were conjugated with fluorescein isothiocyanate for NT or with rhodamine isothiocyanate for GFAP. To explore the influence of STZ injection on microglial and astrocytes, brain sections were incubated with both mouse anti-GFAP (for astrocytes) and biotin-labeled isolectin B4 (for microglia). The secondary antibodies were fluorescein isothiocyanate for GFAP and streptavidin Cy3 for isolectinB4.

Quantification with Image Analysis

Three distinct zones were distinguished in the vicinity of the cortical injection site after icv STZ injection containing astrocytes and microglia with differing morphology. Quantification of microglia and astrocytes in the three zones was made in sections sampled in a range of P0.2-0.8 mm from the bregma. The area of each zone containing the different types of astrocytes was measured and the percentage that each zone occupied in the wound area was calculated (Statistica software, StatSoft, USA). The classes of microglia were counted separately in each zone. The number of cells was divided by the zone area to obtain a measure of cell density.

For each quantitative analysis of NT-immunoreactive astrocytes, 3 sections were sampled from each rat. In 4 brain regions bordering the lateral ventricles and in the CA1 region of the hippocampus NT immunoreactivity was assessed according the following scoring system: 0=No NT-positive astrocytes; 1=NT-positive staining in astrocytic fibers but not in cell bodies; about 7 astrocytes per 40×field; 2=NT-positive staining in astrocytic fibers and in cell bodies; about 20 astrocytes per 40×field; 3=NT-positive astrocytes are present throughout the region; 4=NT-positive astrocytes are present throughout the region and intensely stained.

Cholinesterase and Monoamine Oxidase Activity

The effect of chronic ladostigil treatment on ChE activity in the cortex and hippocampus of rats was determined one week after icv STZ in 12 rats (3 treated with water and 9 with ladostigil). The effect of acute treatment with ladostigil 1 or 17 mg/kg was determined 2 hrs after drug administration. The rats were sacrificed by cervical dislocation, 120 min after the last dose of drug as maximal ChE inhibition was found at this time (Weinstock et al., 2000). The brain was rapidly removed, washed with saline on ice and the cortex, hippocampus and striatum dissected out, quickly weighed and stored at −70° C. until assay. Total ChE activity in the cortex and hippocampus was measured as described in Wang et al., Gender differences in the effect of rivastigmine on brain cholinesterase activity and cognitive function in rats, Neuropharmacology (2000) 39:497-506, using the spectrophotometric method of Ellman et al., A new and rapid colorimetric determination of acetyl-cholinesterase activity, Biochem. Pharmacol. (1961) 7:88-95 with acetylthiocholine (Sigma Ltd) as a substrate using homogenate of 100 mg tissue in 1 ml phosphate buffer. To determine only butyrylcholinesterase (BuChE) activity the amounts of tissue/ml of buffer were increased 3-fold and butyrylthiocholine (Sigma Ltd) was used as a substrate. MAO A and B activity was measured in homogenates of striatum as described in Weinstock et al., Limited potentiation of blood pressure response to oral tyramine by brain-selective monoamine oxidase A-B inhibitor, TV-3326 in conscious rabbits, Neuropharmacology (2002) 43:999-1005.

Object and Place Recognition

Episodic memory in the object recognition test was still intact 2 but not 4 weeks after a single icv STZ injection (Table 3). Therefore, rats that were treated with ladostigil or water were tested for object and place recognition 4 weeks after icv injection of STZ or CSF. The object recognition test measured non-spatial working memory with characteristics of episodic memory that is primarily affected in senile dementia (Bartolini et al., Aniracetam restores object recognition impaired by age, scopolamine, and nucleus basalis lesions, Pharmacol. Biochem. Behav. (1996) 53:277-83). The test depended on intact cortical and hippocampal function (Winters et al., Double dissociation between the effects of peri-postrhinal cortex and hippocampal lesions on tests of object recognition and spatial memory: heterogeneity of function within the temporal lobe, J. Neuroscience (2004) 24:5901-8), while place recognition, another manifestation of spatial memory, was dependent on intact hippocampal function. The experiments were carried out as previously described in Mumby et al., Hippocampal damage and exploratory preferences in rats: memory for objects, places, and contexts, Learning Memory (2002) 9:49-57, in a box made of dark Perspex (60×60 cm and 50 cm high), covered with a dark Perspex lid. In order to increase their interest in the objects, rats were familiarized with the test arena by placing them in it for 5 min on each of 3 successive days and the object recognition test performed on the $4^{th}$ day. Two identical objects were placed in the arena and the time taken by the rats to explore each object during a period of 3 min was recorded. One hour later, the objects were replaced by one that was identical to the two used in the first test and a second one that was different from them and the time taken to explore each of them was again recorded. The following day, the place recognition test was carried out with two identical objects as described above but different from those used previously. One hour later, the one of the two objects was moved to another position in the arena as described in Mumby et al., supra.

Spatial Memory in Water Maze

Two weeks after the place recognition task the rats were tested for spatial memory in the Morris water maze (MWM), which consisted of a circular pool (150 cm in diameter, 60 cm high) filled to depth of 30 cm with water at a temperature of 22±1° C. A transparent glass escape platform (20 cm in diameter) was placed 1 cm below the surface, midway between the centre and rim of the pool in one quadrant where it remained for all the acquisition trials. For data analysis the tank was divided into four quadrants, north (N), south (S), east (E) and west (W). Both collection and analysis of the data were performed using an automated video-tracking system (HVS, Ltd). To begin each trial the rat was placed into the water, facing the maze wall, from one of four start positions evenly spaced around the pool (N, S, E & W). Start positions were chosen randomly at the beginning of each day for all rats. If the rat failed to find the escape platform within 120 s it was placed on it for 10 sec and then removed from the pool. The rat was given two trials a day for 5 days between 10:00 and 14:00 hr with an inter-trial interval of 15 min.

Data Analysis

Group means of 3 measures in the object and place recognition tests, duration of exploration in first and second phases and discrimination index were submitted to one way ANOVA. Mean daily escape latencies for trial 1 and trial 2 in the MWM in each group were analyzed by repeated measures ANOVA for DAY and GROUP followed by Duncan's post hoc test where appropriate. Histological data were analyzed by univariate ANOVA followed by Duncan's post hoc test. All values represent means±SEM.

Results

Changes in Microglia and Astrocytes in Vicinity of Cannula Penetration Site.

Figure 2:
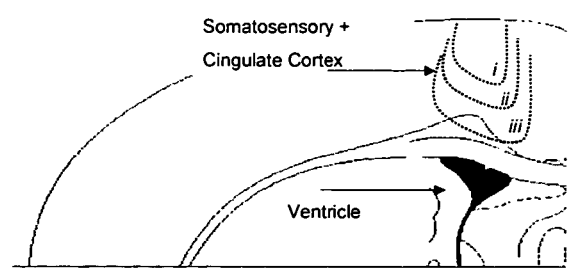
FIG. 2 a) Diagram of brain section showing the three zones in the vicinity of the cannula penetration site with differential microglia and astrocyte activation 7 days after icv STZ.
 b) Microglia: y zones i) microglia have round shaped soma devoid of processes; ii) microglia with polymorphic shaped soma and a variety of fibrous processes; iii) quiescent microglia.
 c) Astrocytes: zones i) astrocyte-free; ii) astrocytes with elongated processes but no soma; iii) reactive astrocytes with thickened processes and filled soma.
 Area box in b) and c) is shown in higher magnification in d) and e) respectively. Calibration bar=100 µm in b) and c) and 20 µm in d) and e).
Figure 2:
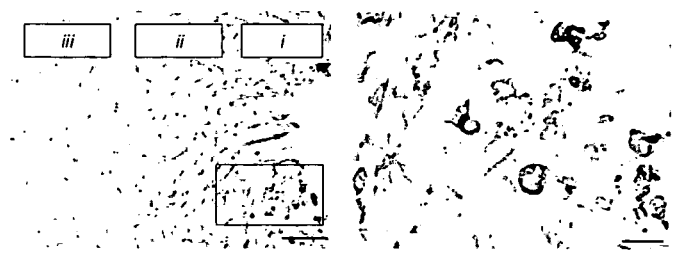
Figure 2:
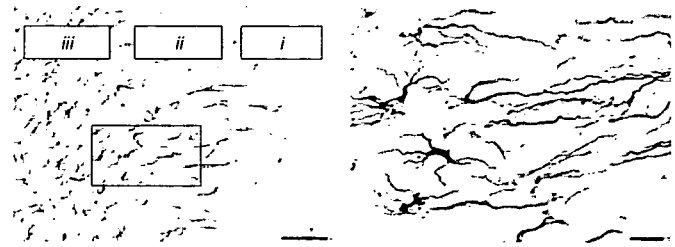
Figure 3:
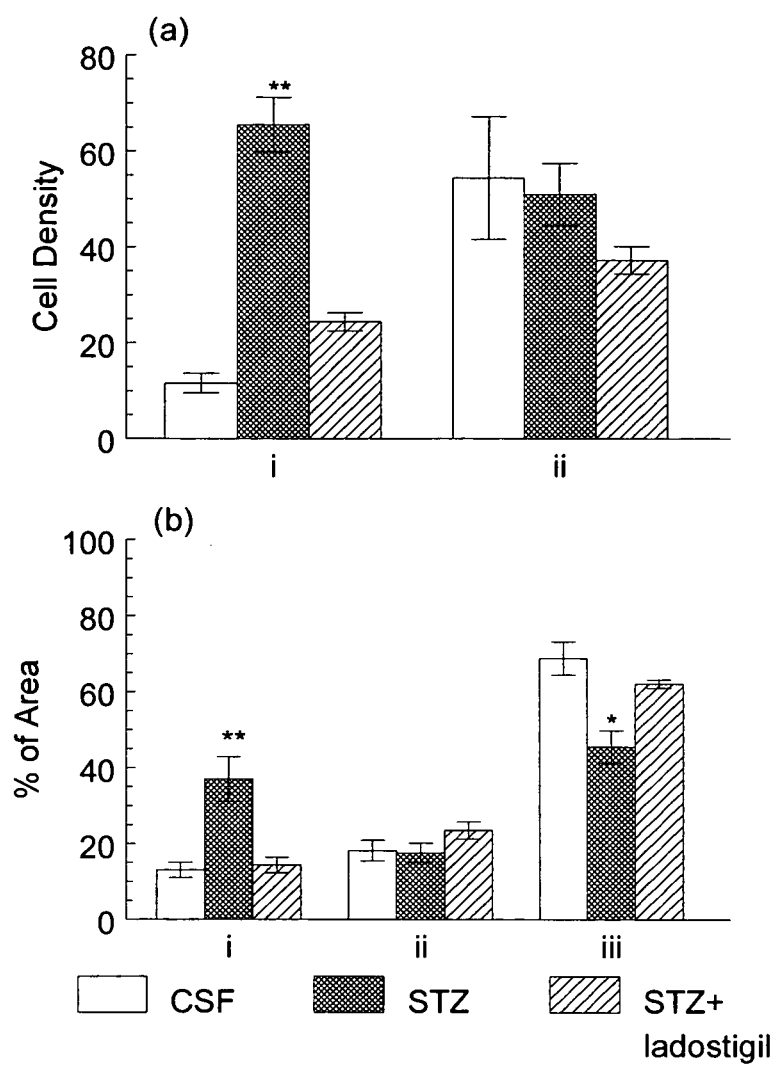
FIG. 3 Quantification of activation of microglia and astrocytes in zones shown in FIG. 2.
 a) Counts of microglia subtypes in zones i) and ii).
 b) % of wound cross sectional area occupied by zones i), ii) and iii).
 In zone (i) the area free of astrocytes is greater in STZ-injected rats. Significantly different from other groups, **P<0.01, *P<0.05.

The three zones of gliosis that could be distinguished in the motor and cingulate cortex close to the cannula penetration site seven days after icv STZ are shown in FIG. 2. Zone i) contained microglia with round shaped soma devoid of processes that resembled macrophages but was almost free of astrocytes; zone ii) had activated microglia with polymorphic shaped soma and a variety of fibrous processes and activated astrocytes with elongated processes but no soma; zone iii) had resident microglia resembling those in the CSF-injected controls and reactive astrocytes with thickened processes and filled soma. Ladostigil prevented the changes both in microglia and in astrocytes in zones i) and iii) that resulted from icv injection of STZ but had no effect on the density of fibrous microglia in zone ii) which was similar to that in CSF-injected controls (FIGS. 3*a, b*).

Figure 4:
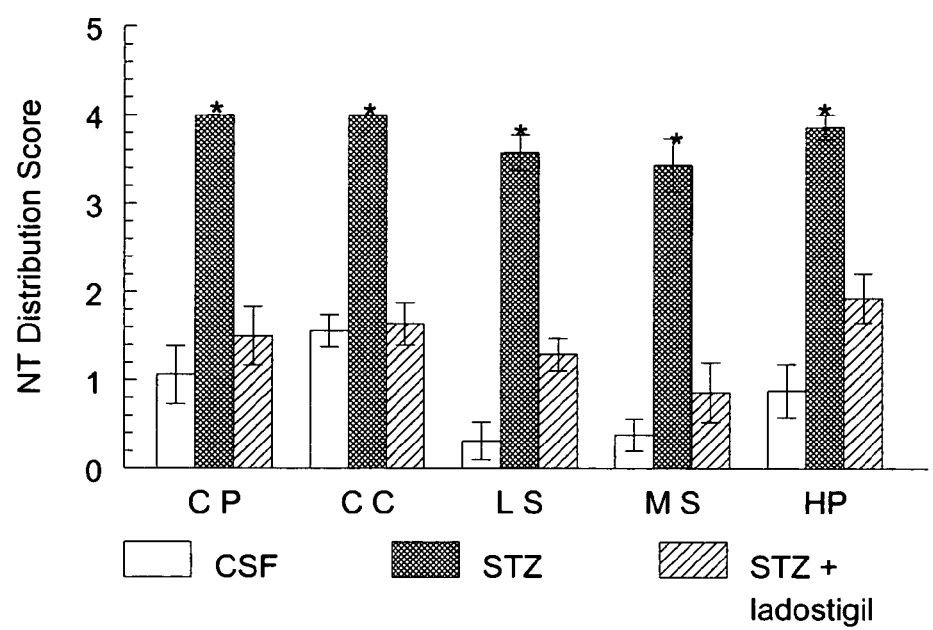
FIG. 4 Quantification of astrocytes with NT expression in cannula penetration site and in three other brain areas bordering the lateral ventricles.
 CP=cannula penetration site; CC=corpus callosum; LS=lateral septum; MS=medial septum HP= hippocampal CA1 area. Significantly different from other groups, *P<0.01.
Figure 5:
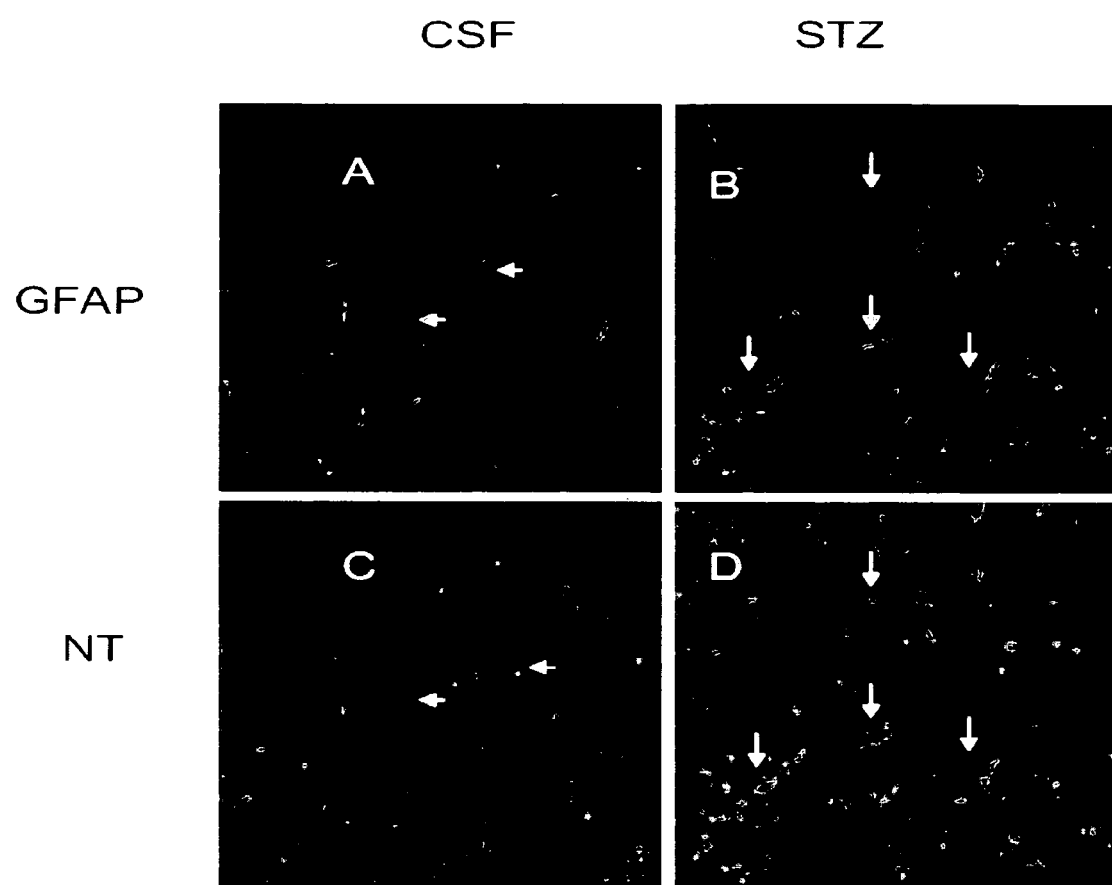
FIG. 5 Confocal picture of NT expression in reactive astrocytes in hippocampus, including localization of NT immunoreactivity in activated astrocytes.
Figure 6:
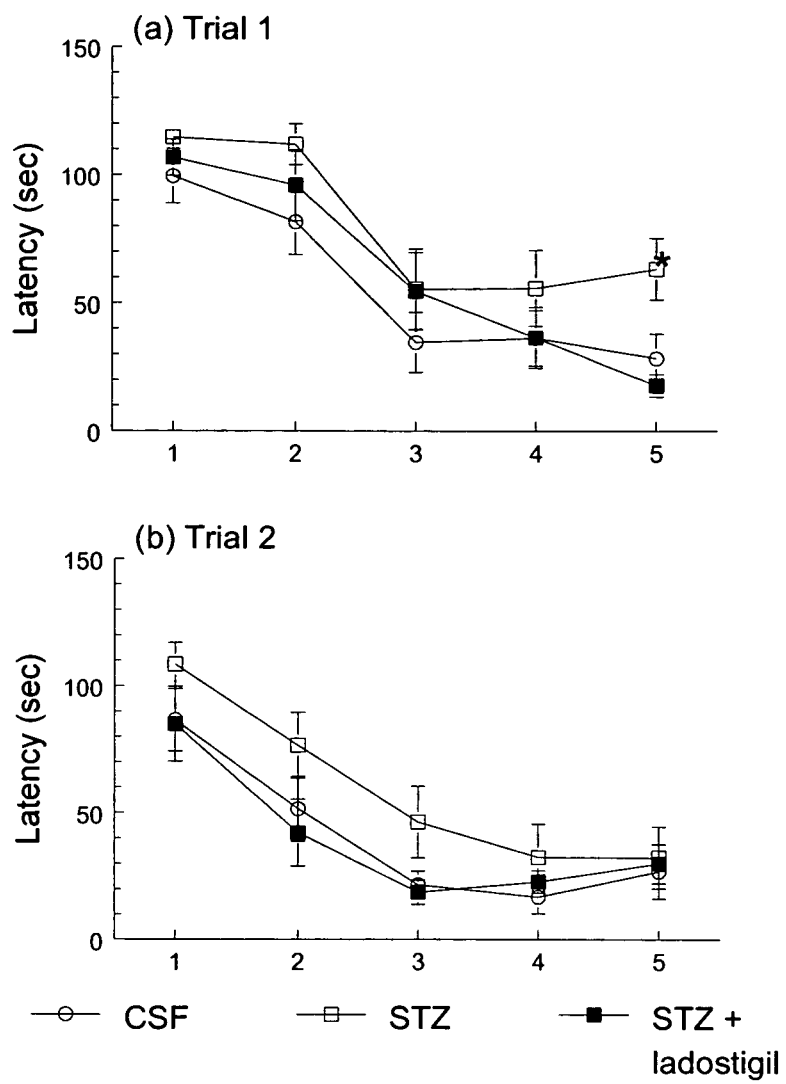
FIG. 6 Effect of ladostigil on spatial memory deficit in the Morris water maze induced by icv STZ. a) trial 1; b) trial 2. Significantly different from other groups *P<0.05.

In the hippocampus, the effect of STZ on glial cells was less well defined. Reactive astrocytes were present in scattered groups most of which were found the CA1 region. They were also seen in the corpus callosum, medial and lateral septum close to the lateral ventricle, while other areas were almost devoid of astrocytes. In all these areas the astrocytes showed a significant increase in NT immunoreactivity (FIGS. 4 and 5). Ladostigil treatment reduced both astrocyte activation and NT immunoreactivity in these brain regions to the level of that seen in CSF-injected controls (FIGS. 4 and 6).

Eight weeks after icv STZ injection, the cannula penetration site contained scar tissue that was filled with tightly packed astrocytic fibers, including the zone previously devoid of them, that were not reactive. Around the scar there were a few reactive astrocytes but no reactive microglia, rounded or fibrous, in or around the scar. No differences were detected in scar morphology in rats injected with icv STZ with or without ladostigil. There were also no signs of NT immunoreactivity in astrocytes in any of the brain regions in which this was present earlier.

Cholinergic Markers

No change in the number or morphology of cholinergic neurons was detected in any of the basal forebrain nuclei, medial septum, diagonal band and nucleus basalis magnocellularis one or eight weeks after icv STZ injection. There was also no change in the density of cholinergic terminals in the hippocampus based on VAChT immuno-reactive varicosities and axonal processes.

Cholinesterase and Monoamine Oxidase Activity

The effect of chronic treatment with ladostigil (1 mg/kg) on total enzyme activity and that of BuChE is shown in Table 2.

TABLE 2

Inhibition of cholinesterase and monoamine oxidase by ladostigil

| Brain region | Time (min) | ChE (%) | BuChE (%) | MAO-A (%) | MAO-B (%) |
|---|---|---|---|---|---|
| Cortex | 60 | 16.1 ± 4.7* | 16.2 ± 2.5* | NT | NT |
|  | 120 | 23.6 ± 3.1* | 15.7 ± 3.2* | NT | NT |
| Hippocampus | 60 | 4.9 ± 2.6 | 7.3 ± 2.5 | NT | NT |
|  | 120 | 5.9 ± 3.2 | 5.4 ± 2.8 | NT | NT |
| Striatum | 60 | NT | NT | 2.8 ± 2.5 | 11.3 ± 1.4* |
|  | 120 | NT | NT | 3.8 ± 2.0 | 15.1 ± 3.4* |
| Plasma | 60 | NT | NT | NT | NT |
|  | 120 | 20 ± 2% | NT | NT | NT |

NT = not tested. Significantly different from untreated rats, *P < 0.05.

A relatively low but significant degree of inhibition was found in the cortex; (24%) of total enzyme activity and 16% of BuChE, seven days after icv STZ and 1 or 2 hrs after the last dose of ladostigil. ChE activity in the plasma was inhibited by 20% However, no significant inhibition of either enzyme was detected in the hippocampus. Ladostigil treatment also had no effect on striatal MAO-A activity and only reduced that of MAO-B by 15% at 2 hrs (Table 2).

Acute administration of ladostigil (1 mg/kg) only inhibited ChE in the cortex by 7.8±1.5% but not in the hippocampus or plasma, while 17 mg/kg inhibited ChE in both brains and in plasma by 40-42%.

Object and Place Recognition

The results of the object and place recognition tests are shown in Table 3.

TABLE 3

Discrimination indices from object[§] and place recognition[‡] tests with different treatments

| Treatment and test (weeks after STZ) | Object | Place |
|---|---|---|
| CSF (2) | 0.342 ± 0.09** | 0.292 ± 0.08** |
| CSF (4) | 0.397 ± 0.05** | 0.274 ± 0.06** |
| " " two days later | 0.339 ± 0.06** | NT |
| STZ (2) | 0.281 ± 0.11* | 0.231 ± 0.08* |
| STZ (4) | −0.175 ± 0.07[#] | 0.000 ± 0.08[#] |
| STZ (4) + ladostigil 1 mg/kg chronic | 0.238 ± 0.05** | 0.211 ± 0.07* |
| STZ (4) + ladostigil 1 mg/kg acute | 0.010 ± 0.08[#] | NT |
| STZ (4) + 17 mg/kg acute | 0.348 ± 0.112** | NT |
| " " two days later | −0.112 ± 0.08[#] | NT |

Data represents the mean ± s.e.m.
[§]Discrimination index = time to explore new object-time to explore familiar object/total exploration time of both objects
[‡]time to explore new position ob object-time to explore original position of object/total exploration time of both objects.
NT = not tested.
Significantly different from 0, **P<0.01, *<0.05;
significantly different from CSF, [#]P<0.01

There were no differences between the groups in the total time spent by the rats exploring both objects in the discrimination phase of the object and place recognition tests. However, rats given icv CSF or icv STZ with ladostigil showed a significant discrimination index in both tests (significantly >0, P<0.05), while those given icv STZ alone failed to do so. This indicates that ladostigil prevents the impairment of episodic and spatial memory induced by icv STZ.

Ladostigil had no effect on the deficit in episodic memory when given at a single dose of 1 mg/kg, four weeks after icv injection of STZ. However, when increased to 17 mg/kg the memory deficit was abolished but returned two days later when ChE was no longer inhibited.

Spatial Memory Test

Repeated measures ANOVA for trial 1 revealed a significant effect of DAY ($F_{4, 26}$=25.67, P<0.0001) but no significant GROUP×DAY interaction. Post hoc test for means for groups over 5 days showed that rats given icv STZ only had significantly higher latencies than those injected with CSF or STZ and treated with ladostigil. In trial 2 there was also a highly significant effect of DAY ($F_{4, 26}$=23.0, P<0.0001), but no DAY×GROUP interaction (FIG. 6). There were also no significant differences between trial 1 and trial 2 in the escape latencies for any day in the different groups of rats, indicating that icv-STZ did not significantly impair working memory in this test.

Discussion

Icv injection of STZ in rats, which has been proposed as a model of the early pathophysiological changes in AD (Arnaiz et al, Impaired cerebral glucose metabolism and cognitive functioning predict deterioration in mild cognitive impairment, Neuroreport (2001) 12:851-5), induces reactive gliosis and oxidative-nitrative stress before the induction of memory deficits and pretreatment with ladostigil can prevent these effects. The reactive gliosis involves both microglia and astrocytes in the cingulate and motor cortex close to the site of cannula penetration, CA1 region of the hippocampus, and in the corpus callosum, medial and lateral septum close to the lateral ventrical. Evidence of oxidative nitrative stress is seen as NT immunoreactivity in astrocytes in the vicinity of cannula penetration, the CA1 area of the hippocampus and regions bordering the lateral ventricles. This is followed 2-5 weeks later by impairment of episodic and spatial memory, although no signs of neuronal damage or reduction in specific cholinergic markers in the cortex or hippocampus are present.

Pretreatment for a week before and one week after icv injection of STZ with ladostigil (1 mg/kg), a novel bifunctional ChE and MAO inhibitor that protects against cytotoxicity induced by a NO donor in cell culture, prevents the microglial activation and loss of astrocytes in the vicinity of the cannula penetration and hippocampal areas and prevents the increase in NT immunoreactivity. Development of memory deficits was prevented three weeks later.

Microglia are very sensitive to changes in their microenvironment and are readily activated in response to infection, brain injury and when the blood brain barrier is breached (McGeer et al., Inflammatory processes in Alzheimer's disease, Prog. Neuro-Psychopharmacol. Biol. Psychiatry (2003) 27:741-9). It was shown that icv injection of STZ greatly increased the number of activated microglia, characterized by shortening of their cellular processes and enlargement of soma, in the vicinity of the cannula penetration site, in the hippocampus and in regions bordering the lateral ventricles. The areas in the cortex and hippocampus showing the highest concentration of activated microglia had a much lower density of astrocytes than in CSF-injected rats. Their disappearance could have been caused by the secretion by microglia of proinflammatory and neurotoxic cytokines, NO and superoxide which are also deleterious to neurons (McCarty et al. 2006). Since astrocytes are important for sequestering glutamate, their loss may have resulted in excess glutamate activity and excitotoxic stress (Lipton and Rosenberg, 1994). In support of this suggestion it has been shown that the glutamate antagonist, memantine reduced the activation of microglia and astrocytes and the memory deficits seen after icv injection of $A\beta_{(1-40)}$ in rats (Miguel-Hidalgo et al., Neuroprotection by memantine against neurodegeneration induced by beta-amyloid (1-40), Brain Res. (2002) 958:210-21).

In an adjacent cortical penetration zone the predominant form of microglia had polymorphic shaped soma with a variety of fibrous processes. These contained a large number of activated astrocytes with long fibrous processes that showed increased GFAP immunoreactivity reminiscent of those induced by ROS and in aging rats (Finch, Neurons, glia, and plasticity in normal brain aging, Neurobiol. Aging (2003) 24:S123-7). The microglia in this zone did not differ in density from those in CSF-injected rats, and suggested that they stimulated the production of GFAP but did not release of cytokines that were toxic to astrocytes.

Activated astrocytes were also seen in different regions of the hippocampus of STZ-injected rats and contained significantly greater amounts of NT than after icv CSF. This may have resulted from the induction of ROS by STZ, like that seen in the pancreas after its parenteral administration (Takasu et al., 1991) and is also seen in aging rodents and human subjects. The NO and superoxide has been shown to alter mitochondrial function and cellular energy in astrocytes and in neighboring neurons (Bolanos et al., Regulation of glucose metabolism by nitrosative stress in neural cells, Mol. Aspects. Med. (2004) 25: 61-73). Similar changes including increased NT immunoreactivity and depressed mitochondrial function are seen in the brains of subjects with AD (Finch, 2003). This could explain the alteration in glucose metabolism induced by icv STZ previously described (Nitsch et al., The intracerebroventricularly streptozotocin-treated rat: impairment of cerebral glucose metabolism resembles the alterations of carbohydrate metabolism of the brain in Alzheimer's disease, J. Neural Transm. (1989) 1:109-10). The increase in GFAP expression in activated astrocytes may also contribute to a reduction in synaptic function, ultimately affecting spatial and episodic memory. The presence of gliosis associated with oxidative-nitrative stress has been reported in AD (Griffin et al., Glial-neuronal interactions in Alzheimer's disease: the potential role of a 'cytokine cycle' in disease progression, Brain Pathol. (1998) 8:65-72) and could result in a suppression of mitochondrial function. Increased GFAP expression in activated astrocytes has been associated with a reduction in synaptic function (Finch, 2003). Thus, the increase in GFAP seen after icv STZ could have contributed to the impairment of spatial (place recognition) and episodic memory (object recognition test) without causing a measurable loss of cholinergic markers. Partial isolation of the cingulate cortex (situated between the bilateral cannulae) induced by icv STZ could also explain the deficit in episodic memory, since the glial scar formed around the cannula penetration site included all cortical layers and the corpus callosum. This scar could disrupt connections of the cingulate cortex to the peri-rhinal cortex which is important for objection recognition (Winters et al., 2004). The constellation of microglial activation, changes in astrocyte morphology and oxidative-nitrative stress that precede the appearance of deficits in glucose metabolism and memory supports the validity of the STZ icv injected rat as a model of the early pathophysiological changes in AD.

Although ladostigil is not an antioxidant, low concentrations have been shown to prevent cytotoxicity induced by ROS and NO in cultured neuronal cells (Youdim and Weinstock, 2001). In the present study, chronic administration of a low dose of ladostigil before and after STZ injection significantly reduced the alterations in microglia and astrocytes prevented the increase in NT immunoreactivity, and three weeks later, the development of episodic memory deficits. It is possible that the prevention by ladostigil of the loss of object recognition resulted from ChE inhibition of 28% in the cortex. However, this cannot explain its effect on place recognition, which depends on hippocampal cholinergic activity and in which no ChE inhibition occurred. It is therefore likely that the neuroprotective effect of ladostigil resulted from other actions of the drug. These could include a direct effect on microglia as shown in preliminary data from experiments in our laboratory in which concentrations of 0.1-10 μM reduced by 20-40% the release of NO from cultured microglia induced by LPS. These concentrations are too low to inhibit ChE in microglia. Ladostigil (0.1-1 μM) also prevented apoptosis in dopaminergic neuroblastoma SH-SY5Y cells exposed to the NO donor Sin1, by reducing 14 the fall in the mitochondrial membrane potential (Maruyama et al., 2003). This action probably does not result from MAO or ChE inhibition since it is shared by other propargylamine-containing aminoindan derivatives that have no effect on these enzymes.

Chronic once daily treatment with ladostigil (1 mg/kg) reduced the number of activated microglia and restored astrocytes in zone (i) of the cannula penetration site after icv STZ injection to those seen after injection of CSF. It also prevented the increase in NT immunoreactivity and development of memory deficits thereby providing an etiological connection between them. The mechanism by which ladostigil produces these anti-inflammatory and neuroprotective effects is not fully understood. One possibility is that it activates α7 nicotinic receptors indirectly as a result of AChE inhibition (Shytle et al., Cholinergic modulation of microglial activation by alpha 7 nicotinic receptors, J. Neurochem. (2004) 89:337-43). Although such an action could possibly contribute to the prevention of gliosis in the cortex in which it produced about a 20% inhibition of AChE, it cannot explain the marked reduction in NT immunoreactivity and astrocyte activation in the hippocampus in which no significant AChE inhibition occurred. Neither does the neuroprotection result from MAO-B inhibition which did not exceed 15%. A more likely explanation is that ladostigil reduces apoptosis and cell death in both neurons and astrocytes by preventing the fall the mitochondrial membrane potential induced by NO and superoxide anion released from microglia (Takuma et al., Astrocyte apoptosis: implications for neuroprotection, Prog. Neurobiol. (2004) 72:111-127). Such an action of ladostigil was demonstrated in dopaminergic neuroblastoma SH-SY5Y cells exposed to the NO donor, Sin1.

Acute administration of ladostigil (1 mg/kg) that only inhibited ChE by about 8% was unable to reverse the memory deficits once they had occurred. This was achieved by a larger dose that inhibited cortical ChE by 40%. The data suggest that prevention of gliosis, oxidative-nitrative stress and memory deficits induced by chronic administration of a low dose of ladostigil results from a combination of actions on neuronal and glial cells. The ability to inhibit ChE may contribute to the effect on episodic memory.

Example 3

The clinical condition of mild cognitive impairment (MCI) is one in which persons experience memory loss which is greater than what would be expected for their age (Petersen et al., 2001). A significant proportion of subjects with MCI develop dementia of the Alzheimer type (AD) within a few years. ChE inhibitors slow the progression of cognitive impairment in AD, but it is not yet known whether they can delay or prevent the progression of MCI to AD. Like humans, rats develop an age-related memory loss that is associated with a reduction in the number and size of cholinergic nerve terminals on cortical pyramidal cells (Turrini et al., 2001, Casu et al., 2002). At the age of 18 months, rats already show a 40-50% reduction in ACh release in the cortex and hippocampus. This can be increased to normal levels by acute administration of ChE inhibitors in doses that improve their memory deficits (Scali et al., 2002). However, it is not known whether any ChE inhibitor, and ladostigil in particular, can prevent the progression to memory impairment in aged rats; nor is it known what dosage would be effective.

Experiments were performed in 30 male rats of the Wistar strain. At the age of 16 months 80% of them showed intact object recognition, compared to 90% of those aged 3 months. The rats were housed in pairs at an ambient temperature of 21° C. They were weighed once weekly and their fluid intake measured daily for two weeks and then twice weekly for the remaining 4 months. Ten of the rats were started on ladostigil 1 mg/kg/day in the drinking fluid when aged 16 months and given the drug for four months. The remaining 10 rats of the same age were given regular drinking water. At the end of the four months spatial memory of these 20 rats and of another 10 aged 3 months was tested in the Morris water maze as previously described (Shoham et al, 2006).

Figure 7:
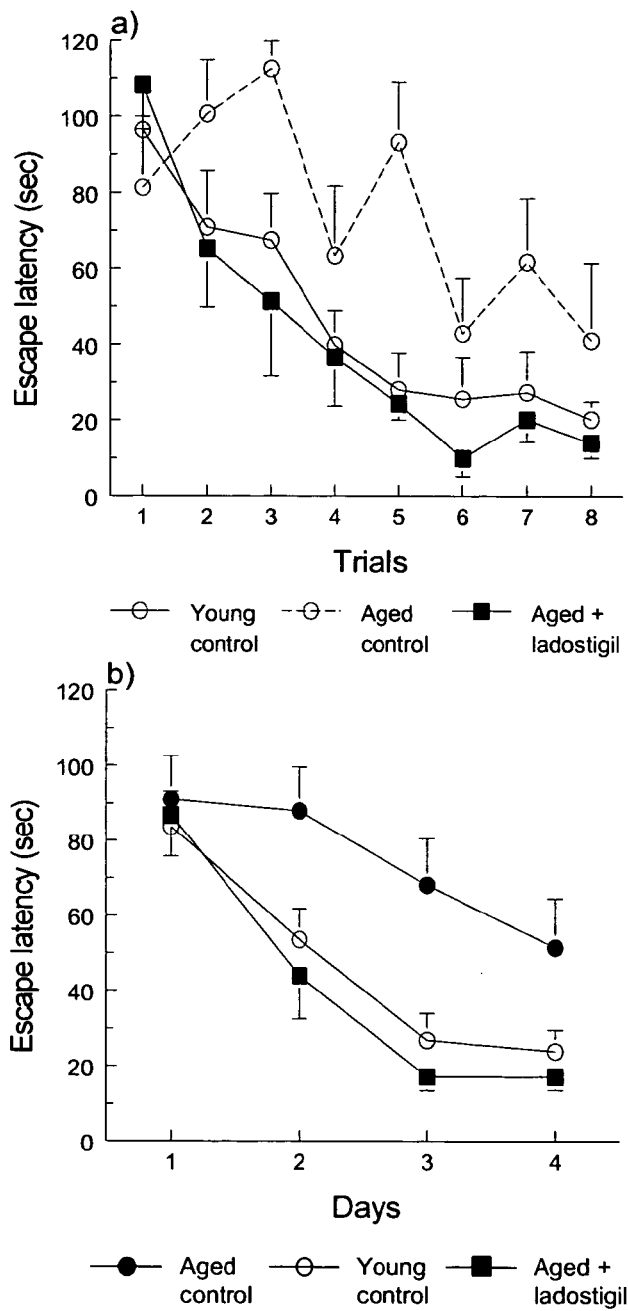
FIG. 7 Comparison of spatial learning in young and old rats in the Morris water maze(MWM). Prevention by 1 mg/kg of ladostigil of learning deficits in old rats; a) shows escape latency on each of two daily trials. Note much larger day-day variability in escape learning in aged untreated rats that is prevented by chronic treatment with ladostigil; b) average escape latency for two daily trials.

The aged untreated rats showed a significantly slower acquisition of spatial learning than the young rats. The difference in learning between young and old rats was substantially abolished by low dose ladostigil treatment (FIG. 7 a, b). The data show that chronic treatment with a low dose of ladostigil can prevent the development of memory deficits in aged rats.

Discussion

Mild cognitive impairment (MCI) is a condition generally characterized by mild recent memory loss without dementia or significant impairment of other cognitive functions. MCI causes memory problems that are greater than normally expected with aging, but a person with MCI does not show other symptoms of dementia, such as impaired judgment or reasoning. The causes of MCI are not well understood. An advisory panel to the US Food and Drug Administration ruled in 2001 that MCI, a condition separate from Alzheimer's disease, is a valid target for new drug therapies. The Peripheral and Central Nervous System Drugs Advisory Committee has stated that more than 80% of patients with mild cognitive impairment develop Alzheimer's disease within 10 years. Scientists are still working to understand MCI and its relationship to Alzheimer's disease. Because basic questions about this disorder remain to be answered, the definition of MCI continues to evolve. (Mild Cognitive Impairment-Alzheimer's Part XVI, Harold Rubin, MS, ABD, CRC, Nov. 14, 2006).

Mild cognitive impairment has recently been shown to exist in two distinct subtypes: neurodegenerative MCI and vascular MCI. Subjects with neurodegenerative MCI exhibit medial temporal lobe atrophy, while subjects with vascular MCI present with vascular lesions, both of which be observed by magnetic resonance imaging (MRI). It has recently been reported that neurodegenerative MCI subjects possess impaired cognitive domains involving memory, which is found to be predictive for conversion to dementia or Alzheimer's disease (Meyer et al., 2005). Until recently, little evidence to support the hypothesis that MCI was a precursor for Alzheimer's existed; however, Meyer et al. clearly teach that MCI can take the form of a neurodegenerative disorder and later take the form of dementia or Alzheimer's.

What is claimed is:

1. A method of slowing the progression of a neurodegenerative disease diagnosed as mild cognitive impairment (MCI) to a more advanced stage of the neurodegenerative disease in an afflicted subject, comprising administering to the subject an amount of R(+)-6-(N-methyl,N-ethyl-carbamoyloxy)-N-propargyl-1-aminoindan or a salt thereof effective to slow the progression of the disease, with the effective amount being no more than 0.37 mg/kg/day of the subject.

2. The method of claim 1, wherein the effective amount administered to the subject causes no more than 30% MAO inhibition and no more than 30% ChE inhibition.

3. The method of claim 1, comprising administration of a salt of R(+)-6-(N-methyl, N-ethyl-carbamoyloxy)-N-propargyl-1-aminoindan.

4. The method of claim 3, wherein the salt of R(+)-6-(N-methyl,N-ethyl-carbamoyloxy)-N'-propargyl-1-aminoindan is the tartrate salt.

5. The method of claim 1, wherein the subject is a human.

6. The method of claim 5, wherein the MCI is characterized by age-related memory loss without dementia and which is greater than expected for the subject's age.

7. The method of claim 6, wherein the salt is the tartrate salt and the corresponding amount of the tartrate salt is no more than 0.46 mg/kg/day of the subject.

8. The method of claim 1, wherein the MCI is neurodegenerative MCI or vascular MCI.

9. The method of claim 1, wherein the MCI is characterized by medial temporal lobe atrophy or vascular lesions observed by magnetic resonance imaging (MRI).

10. The method of claim 5, wherein the amount of R(+)-6-(N-methyl,N-ethyl-carbamoyloxy)-N'-propargyl-1-aminoindan or a salt thereof administered is 10 mg/day to 25 mg/day.

11. The method of claim 5; wherein the amount of R(+)-6-(N-methyl,N-ethyl-carbamoyloxy)-N'-propargyl-1-aminoindan or a salt thereof administered is 0.14 mg/kg/day to 0.37 mg/kg/day of the subject.

12. The method of claim 11, wherein the amount of R(+)-6-(N-methyl,N-ethyl-carbamoyloxy)-N-propargyl-1-aminoindan or a salt thereof administered is 0.15 mg/kg/day of the subject.

13. The method of claim 1, wherein the method slows the progression of mild cognitive impairment to dementia and the dementia is static dementia, senile dementia, presenile dementia, progressive dementia, vascular dementia or Lewy body dementia.

14. The method of claim 1, wherein the method slows the progression of mild cognitive impairment to Alzheimer's disease.

15. The method of claim 1, wherein the method prevents the appearance of symptoms of the neurodegenerative disease in a subject predisposed to the disease.

16. A method of treating a subject afflicted with a neurodegenerative disease diagnosed as mild cognitive impairment (MCI), the method comprising administering to the subject an amount of R(+)-6-(N-methyl,N-ethyl-carbamoyloxy)-N-propargyl-1-aminoindan or a salt thereof effective to treat the subject.

17. The method of claim 16, wherein the amount is no more than 0.37 mg/kg/day of the subject.

18. The method of claim 16, wherein the MCI is characterized by age-related memory loss which is greater than expected for the subject's age without dementia.

19. The method of claim 16, wherein the MCI is characterized by medial temporal lobe atrophy or vascular lesions observed by magnetic resonance imaging (MRI).

20. The method of claim 16, wherein the MCI is selected from neurodegenerative MCI and vascular MCI.

\* \* \* \* \*

UNITED STATES PATENT AND TRADEMARK OFFICE
CERTIFICATE OF CORRECTION

PATENT NO.        : 8,420,696 B2
APPLICATION NO.   : 11/637600
DATED             : April 16, 2013
INVENTOR(S)       : Weinstock-Rosin et al.

Page 1 of 1

It is certified that error appears in the above-identified patent and that said Letters Patent is hereby corrected as shown below:

Title Page:
Item (73) Assignees, after "Yissum Research Development Company of the Hebrew University of Jerusalem, Jerusalem", please insert -- (IL) --.

In the Claims:

Column 24:
Line 15 (claim 1, line 6), please change "oyloxy)-N-propargyl-1-aminoindan" to
-- oyloxy)-N'-propargyl-1-aminoindan --.

Line 22 (claim 3, line 2), please change "R(+)-6-(N-methyl,N-ethyl-carbamoyloxy)-N-propar-" to
-- R(+)-6-(N-methyl,N-ethyl-carbamoyloxy)-N'-propar- --.

Line 48 (claim 12, line 2), please change "6-(N-methyl,N-ethyl-carbamoyloxy)-N-propargyl-1-ami-"
to -- 6-(N-methyl,N-ethyl-carbamoyloxy)-N'-propargyl-1-ami- --.

Line 65 (claim 16, line 4), please change "R(+)-6-(N-methyl,N-ethyl-carbamoyloxy)-N-" to
-- R(+)-6-(N-methyl,N-ethyl-carbamoyloxy)-N'- --.

Signed and Sealed this
Second Day of July, 2013

Teresa Stanek Rea
*Acting Director of the United States Patent and Trademark Office*